United States Patent
Rise

(10) Patent No.: US 6,176,242 B1
(45) Date of Patent: Jan. 23, 2001

(54) METHOD OF TREATING MANIC DEPRESSION BY BRAIN INFUSION

(76) Inventor: Mark T. Rise, 7745 Aetna Ave. NE., Monticello, MN (US) 55432

(*) Notice: Under 35 U.S.C. 154(b), the term of this patent shall be extended for 0 days.

(21) Appl. No.: 09/302,591

(22) Filed: Apr. 30, 1999

(51) Int. Cl.$^7$ .................................................. A61B 19/00
(52) U.S. Cl. ............................................. 128/898; 607/2
(58) Field of Search ..................... 128/898; 604/891.1, 604/890.1, 65–67; 607/2, 45, 48; 600/378

(56) References Cited

U.S. PATENT DOCUMENTS

| | | |
|---|---|---|
| 4,346,709 | 8/1982 | Schmitt . |
| 4,596,807 | 6/1986 | Cosby . |
| 4,692,147 | 9/1987 | Duggan . |
| 4,698,342 | 10/1987 | Crosby . |
| 4,892,538 | 1/1990 | Aebischer et al. ............. 604/891.1 |
| 4,912,126 | 3/1990 | Owen . |
| 4,980,174 | 12/1990 | Sagen et al. . |
| 5,119,832 | 6/1992 | Xavier . |
| 5,259,387 | 11/1993 | de Pinto . |
| 5,280,793 | 1/1994 | Rosenfeld . |
| 5,299,569 | 4/1994 | Wernicke et al. ................. 607/45 |
| 5,330,768 | 7/1994 | Park et al. ......................... 424/501 |
| 5,458,629 | 10/1995 | Baudino et al. .................. 607/116 |
| 5,458,631 | 10/1995 | Xavier ............................... 607/117 |
| 5,470,846 | 11/1995 | Sandyk ............................. 514/159 |
| 5,540,734 | 7/1996 | Zabara ................................ 607/96 |
| 5,599,560 | 2/1997 | Siuciak ............................... 424/570 |
| 5,711,316 | * 1/1998 | Elsberry et al. ..................... 128/898 |
| 5,833,709 | * 11/1998 | Rise et al. ............................ 607/2 |

OTHER PUBLICATIONS

Emily E. Meuller, Robert Loeffel and Sedgwick Mead, "Skin Impedance in Telation to Pain Threshold Testing by Electrical Means" published in J. Applied Physiology 5, 746–752, 1953.

Medtronic SynchroMed® EL Infusion System.

Medtronic Itrel II Implantable Pulse Generator (IPG) Model 7424.

Craig G. van Horne, Spencer Bement, Barry J. Hoffer, Greg A. Gerhardt, "Multichannel semiconductor–based electrodes for in vivo electrochemical and electrophysiological studies in rat CNS" *Neuroscience Letters*, 120 (1990) 249–252.

Harris Corporation Model CDP 1878 frequency generator.

* cited by examiner

*Primary Examiner*—Mickey Yu
*Assistant Examiner*—Kelly O'Hara
(74) *Attorney, Agent, or Firm*—Curtis D. Kinghorn; Harold R. Patton

(57) ABSTRACT

Techniques using one or more drugs, electrical stimulation or both to treat depression or manic depression by means of an implantable signal generator and electrode and/or an implantable pump and catheter. A catheter is surgically implanted in selected sites in the brain to infuse the drugs, and one or more electrodes are surgically implanted in the brain at selected sites to provide electrical stimulation.

9 Claims, 19 Drawing Sheets

METHOD OF TREATING MANIC DEPRESSION BY BRAIN INFUSION

BACKGROUND OF THE INVENTION

1. Field of the Invention

This invention relates to nerve tissue stimulation and infusion techniques, and more particularly relates to such techniques for treating depression and manic depression.

2. Description of the Related Art

A persons immediate emotional state is referred to as their affective state. Two normal emotions or affective states are eurphoria and depression. These affective states are experienced transiently by all persons in response life situations. For some individuals however, these normal emotional responses may become sustained for long periods of time. The general affective state may not reflect the momentary expeiences of the individual. Two affective disorders involving the emotions of eurphoria and depression are unipolar or major depression and bipolar depression or manic depression.

Unipolar depression manifests as episodes of dysphoria (unpleasant mood) and anhedonia (inability to experience pleasure) which may last for months. Symptoms may include a loss of energy, changes in weight (most often weight loss but possibly weight gain) insomnia or sometimes oversleeping, restlessness, and inability to concentrate, loss of sex drive, negative thoughts, feelings of worthlessness and suicidal ideation. Unipolar depression is characterized by subtypes. The estimates are that there may be as many as 4 million people in the United States suffering from depression.

Persons with bipolar depression will experience depressive episodes just as those suffering from major depression. These episodes are clinically indistiguishable form those described above. However, they will also experience episodes of mania. Manic episodes are characterized by a prolonged state of euphoria. The person is full of energy with a decreased need for sleep, will have rapid speech and feels grandiose. He or she may have an increased libido and engage in reckless involvements. In severe cases the patient may be delusional and experience hallucinations. Some persons will switch between the two affective states quickly, within a matter of minutes.

Depression can be treated with oral medications. Examples are the monoamine oxidase inhibitors, such as phenelzine, serotonin uptake blockers like trazodone and fluoxetine and trycyclinc compounds like imipramine. Lithium salts are used to terminate manic episodes and prophylactically to prevent reaccurance. Antipsychotic drugs can be used in combination with tricyclics for cases of depression when psychosis is present.

Siuciak (5,599,560) discloses the use of neurotrophins to treat depression. Cosby (4,596,807; 4,698,342) teaches the use of the serotonin precursor l-tryptophan. Owen (4,912, 126) discloses the use of 3(H)-indolones. Sgan (4,980,174) describes implanting monoamine producing living cells into the central nervous system to treat depressive patients.

The use of biofeedback to the user of the asymmetry between the brain waves measured at two locations as a means of treating depression is disclosed by Rosenfeld (5,280,793).

Electrical stimulation of the nervous system has been proposed as a therapeutic treatment of depression. Sandyk (5,470,846) disclosed the use of transcranial pulsed magnetic fields to treat depression. Werneke et. al. (5,299,569) discloses electrical stimulation of the vagus nerve and Zabara (5,540,734) teaches stimulation of the trigeminal or glossopharyngeal nerves for psychiatric illness such as depression.

SUMMARY OF THE INVENTION

A preferred form of the invention uses one or more drugs and/or electrical stimulation to treat an depression. The treatment is carried out by an implantable pump and a catheter having a proximal end coupled to the pump and having a discharge portion for infusing therapeutic dosages of the one or more drugs into a predetermined infusion site in brain tissue. Alternatively, encapsulated cells selected to secrete the appropriate substance or a drug eluting polymer may be implanted into a predetermined treatment site in brain tissue. The treatment also may be carried out by an implantable signal generator and an implantable electrode having a proximal end coupled to the signal generator and having a stimulation portion for electrically stimulating a predetermined stimulation site in the brain tissue. In one embodiment of the invention stimulation and/or infusion is carried out in a nearly continuous manner. In another form of the invention, the stimulation or infusion is initiated by the patient in response to undesirable symptoms associated with depression or mania.

1. Another form of the invention uses a sensor in combination with the signal generator, one or more stimulating electrodes, pump and catheter to treat a neurological disorder. In this form of the invention, the sensor generates a sensor signal related to a condition resulting from the depressive or manic disorder. Control means responsive to the sensor signal regulate the signal generator and pump so that the neurological disorder is treated.

By using the foregoing techniques, the symptoms of the unipolar and bipolar depressive disorders can be controlled to a degree unattainable by prior art methods or apparatus.

BRIEF DESCRIPTION OF THE DRAWINGS

These and other advantages and features of the invention will become apparent upon reading the following detailed description and referring to the accompanying drawings in which like numbers refer to like parts throughout and in which.

DESCRIPTION OF THE PREFERRED EMBODIMENTS

Figure 1:
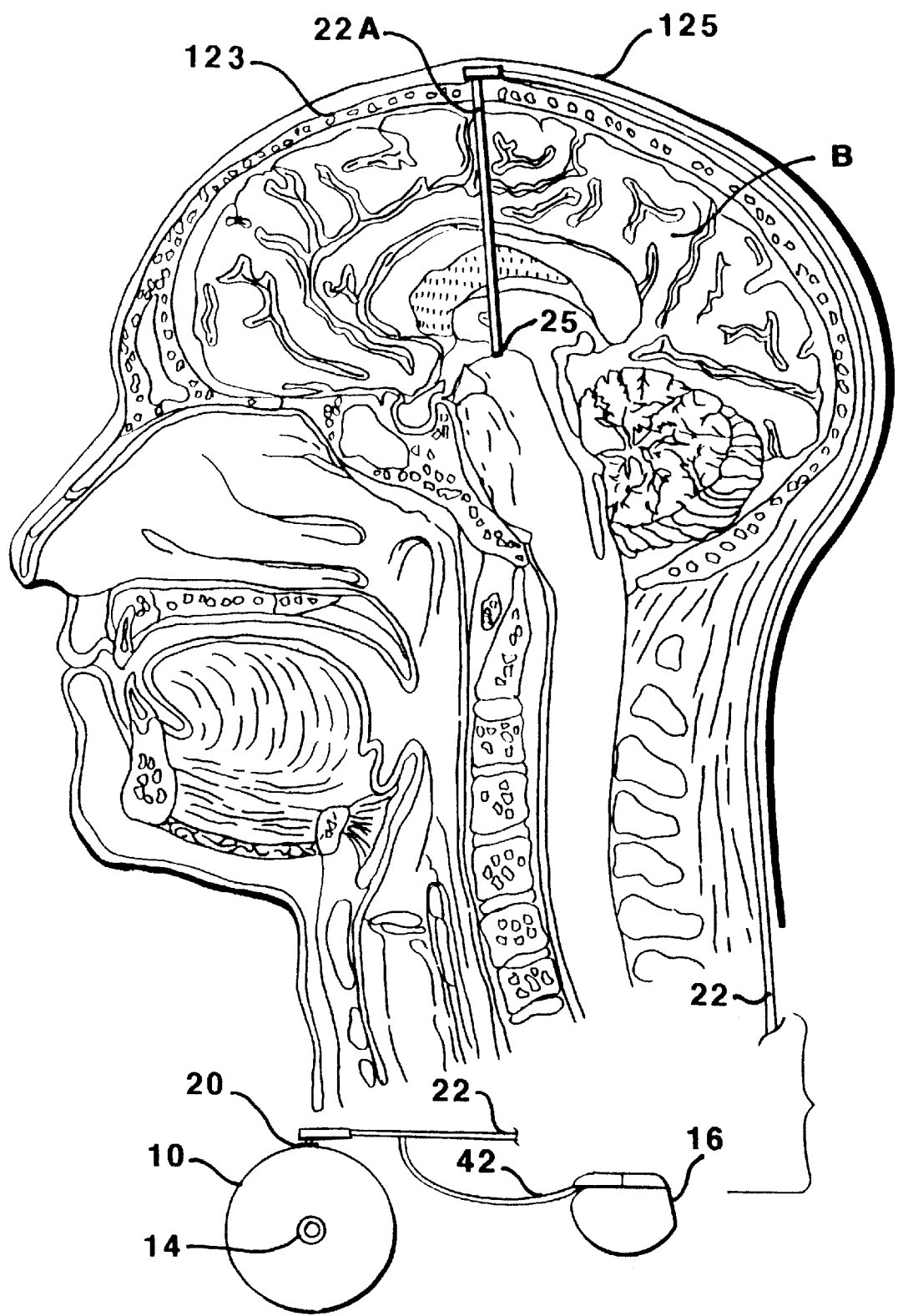
FIG. 1 is a diagrammatic illustration of a combined catheter and electrode implanted in a brain according to a preferred embodiment of the present invention, and a signal generator and pump coupled to the combined catheter and electrode.

Referring to FIG. 1, a pump or device 10 made in accordance with the preferred embodiment may be implanted below the skin of a patient. The device has a port 14 into which a hypodermic needle can be inserted through the skin to inject a quantity of a liquid agent, such as a medication or drug. The liquid agent is delivered from device 10 through a catheter port 20 into a catheter 22. Catheter 22 is positioned to deliver the agent to specific infusion sites in a brain (B). Device 10 may take the form of the like-numbered device shown in U.S. Pat. No. 4,692,147 (Duggan) ("the '147 Patent"), assigned to Medtronic, Inc., Minneapolis, Minn., which is incorporated by reference. An embodiment of pump 10 may be found in the Synchromed™ Infusion System manufactured by Medtronic, Inc. of Minneapolis, Minn. However, pump 10 may take the form of any device used for moving fluid from a resevoir.

The distal end of catheter 22 terminates in a cylindrical hollow tube 22A having a distal end 25 implanted into a portion of the brain by conventional stereotactic surgical techniques. A semispherical portion 23 (FIG. 3) at the distal end 25 of tube 22A provides a rounded profile for minimizing tissue disruption during insertion. End 25 is provided with microporous portions 27–29 (FIG. 3) to allow infusion and filtering of a liquid agent. Microporous portions 27–29 are preferably composed of a porous material such as polysulfone hollow fiber, manufactured by Amicon, although polyethylene, polyamides, polypropylene and expanded polytetrafluorethylene (ePTFE) are also suitable.

In a preferred embodiment, the preferred pore size is approximately less than or equal to 0.22 microns. It is preferred that the maximum pore size be less than or equal to approximately 0.22 microns to prevent any derelict bacterial agents that may be present inside the catheter 22A from entering into the brain B. Furthermore, at larger pore sizes, there is the potential for tissue in-growth that may restrict the flow of agents out of the microporous portions 27–29. Alternatively, end 25 may be provided with multiple holes or slits in which case filtering of the liquid agent may occur within pump 10.

Catheter 22 could take the form of a lead catherter combination developed for use outside of the dural covering of the spinal cord to treat pain which is shown in FIG. 1 in U.S. Pat. No. 5,423,877 (Mackey) which is incorporated by reference. Alternatively, catheter 22 could take the form depicted in FIGS. 1–4 in U.S. Pat. Nos. 5,119,832 and 5,458,631 (Xavier) which is incorporated by reference also developed for use outside of the dura to treat pain in which the center lumen 34 terminates in a single opening at the distal end 25 of catheter 22A Referring to FIG. 2, tube 22A includes an outer cylindrical insulating jacket 30 and an inner cylindrical insulating jacket 32 that defines a cylindrical catheter lumen 34. A multifilar coil of wire 36 is embedded in tube 22A as shown. Alternatively, wire 36 could consist of multifilar stranded wire.

When selecting the tube 22A used with a particular drug or agent, care should be taken to ensure that the particular agent will be compatible with the material from which the inner cylindrical insulating jacket 32 is composed. The inner cylindrical insulating jacket 32 and outer cylindrical insulating jacket 30 should be sufficiently flexible to facilitate insertion. The outer cylindrical insulating jacket 30 should be biocompatible. While it is desirable to have the inner insulating jacket 32 be biocompatible it may not be absolutly necessary provided the inner insulating layer can be kept from contacting the biological tissue. An enhanced tear resistant silicone elastomer or polyurethane are examples of materials that could be used. A durometer shore value of 80 is preferred.

Tube 22A is surgically implanted through a hole in the skull 123 and catheter 22 is implanted between the skull and the scalp 125 as shown in FIG. 1. A stylet may be placed into the center of tube 22A to give it stiffness when introducing the tube into the brain. After the stylet is removed, center lumen 34 constitutes a catheter which can be used to infuse an agent, including a drug. Catheter 22 is joined to implanted device 10 in the manner shown. Tube 22A may be continuous with tube 22 or there may be an interveining connection most likely at the burr hole or located somewhere along the subcutaneous path.

Catheter 22 may be divided into twin tubes, tube 22A and a second tube (not shown), that are implanted into the brain bilaterally. Alternatively, the second tube may be supplied with drugs from a separate catheter and pump and with electrodes from a separate signal generator.

Referring again to FIG. 1, a system or device 16 made in accordance with the preferred embodiment also may be implanted below the skin of a patient. Device 16 may take the form of a signal generator Model 7424 manufactured by Medtronic, Inc. of Minneapolis, Minn. under the trademark Itrel II.

Figure 2:
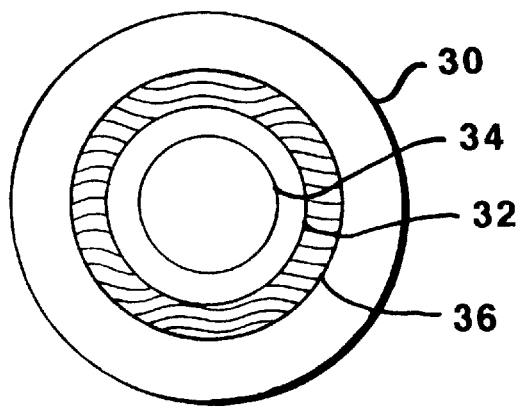
FIG. 2 is a cross-sectional view of the catheter-electrode of FIG. 1 taken along line 2—2 of FIG. 3.
Figure 3:
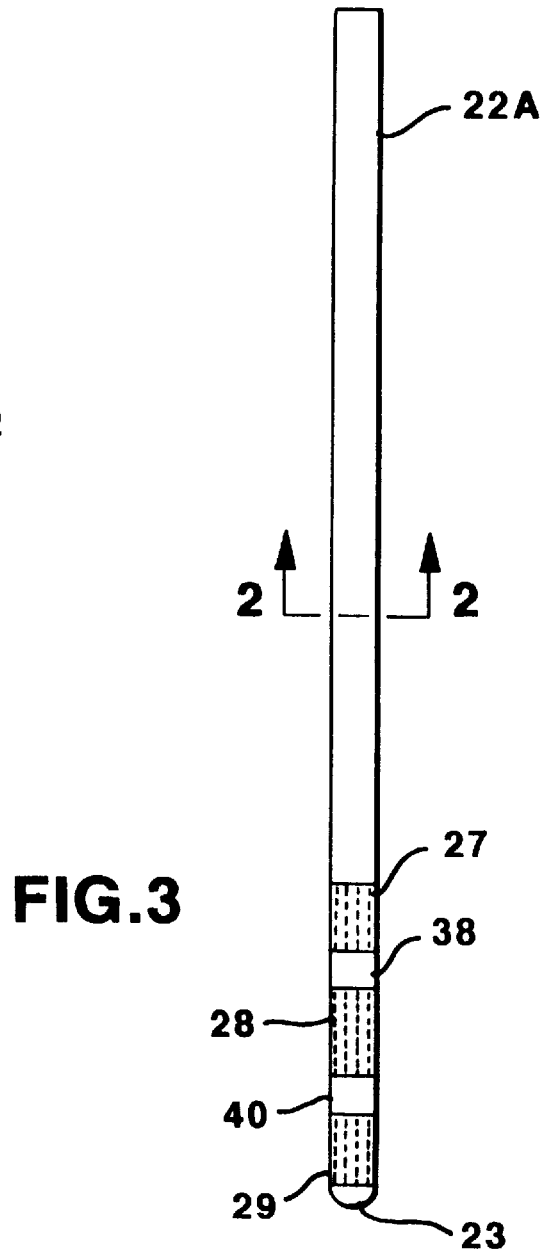
FIG. 3 is a diagrammatic view of the catheter-electrode shown in FIG. 1.

The distal end of tube 22A terminates in stimulation electrodes 38 and 40 (FIG. 3). Each of electrodes 38 and 40 is individually connected to device 16 through a conductor in wire bundle 36 (FIG. 2). The wires exit catheter 22 to form a cable 42 which is joined to implanted signal generator 16 in the manner shown in FIG. 1. While the preferred embodiment shows two electrodes on tube 22A (FIG. 3), some brain locations may require a greater number. In addition, tube 22A may have only one electrode using a portion of the case of the signal generator 16 (FIG. 1) as the reference electrode. Furthermore, in some instances infusion conduit 34 (FIG. 2) and conductor conduit 36 may not be concentric tubes but rather separate conduits located beside each other in a common tube as is embodied in FIG. 6 of U.S. Pat. No. 5,458,629 (Baudino et. al.), incorporated by reference.

Signal generator 16 is implanted in a human body, preferably in a subcutaneous pocket located over the chest cavity or the abdomen. While showed as separate devices in FIG. 1, devices 10 and 16 could be incorporated into a common device.

The present invention may preferably be implemented by providing seven different drug dosages from 0 dosage to a 1.0 ml dosage with 0.1 ml increments between choices. The time interval between dosages can preferably be selected between one and twelve hours in seven choices. This is the same type of dosage and interval described in connection with device 10 shown in the '147 Patent (column 5, beginning at line 63). The seven drug dosages and corresponding time increments may be loaded into RAM 102a (FIG. 11B of the '147 Patent). The selected dosage and interval of a drug is then delivered, as described in the '147 Patent, through catheter 22 and tube 22A to a selected location in the brain appropriate for the treatment of anxiety disorders.

The type of drugs administered by device 10 into the brain depend on the specific location at which distal end 25 of tube 22A is surgically implanted. They also depend on whether treatment is for symptoms of depression or symptoms of mania. The appropriate brain location to surgically implant distal end 25, the desired action on the neurons at that location and the types of drug agents useful at that location are provided in the following Table I:

TABLE I

| BRAIN LOCATION | DESIRED ACTION | TYPES OF AGENTS |
|---|---|---|
| TREATMENT OF MANIC SYMPTOMS | | |
| Anterior Limb of Internal Capsule | Decrease neuronal activity | Anesthetic |
| Nucleus Accumbens | Decrease neuronal activity | GABA Agonist Dopamine Antagonist |
| Cingulum fibers | Decrease neuronal activity | Anesthetic |
| Cingulate Gyrus | Decrease neuronal activity | GABA Agonist |
| Dorsal Medial Nucleus of Thalamus | Decrease neuronal activity | Serotonin Antagonist GABA Agonist |
| Locus Coeruleus | Decrease neuronal activity | Adrenergic Antagonist GABA Agonist |
| Dorsal raphe Nucleus | Decrease neuronal activity | GABA Agonist Serotonin Antagonist |
| Frontal Cortex | Decrease neuronal activity | Glutamate antagonist GABA Agonist |
| TREATMENT OF DEPRESSIVE SYMPTOMS | | |
| Nucleus Accumbens | Decrease neuronal activity | GABA Antagonist Dopamie Agonist |
| Cingulate Gyrus | Decrease neuronal activity | GABA Antagonist |
| Dorsal Medial Nucleus of Thalamus | Increase neuronal activity | Serotonin Agonist GABA Antagonist |
| Locus Coeruleus | Increase neuronal activity | Adrenergic Agonist GABA Antagonist |
| Dorsal Raphe Nucleus | Increase neuronal activity | GABA Antagonist Serotonin Agonist |
| Frontal Cortex | Increase neuronal activity | Glutamate Agonist GABA Antagonist |

Coordinates for the portions of the brain described in Table I are as follows:

TABLE II

| BRAIN REGION | MEDIAL-LATERAL DIMENSION | DORSAL-VENTRAL DIMENSION | ANTERIOR-POSTERIOR DIMENSION |
|---|---|---|---|
| Dorsal Medial Nucleus of Thalamus | 0.0 to 1.0 | 0.2 to 1.7 | 0.1 to −1.1 |
| Anterior Limb of Internal Capsule | 1.8 to 2.0 | 0.2 to −0.2 | 2.2 to 2.9 |
| Cingulum fibers | 0.0 to 1.0 | 2.0 to 3.0 | 0.0 to 4.5 |
| Cingulate Gyrus | 0.0 to 1.5 | 2.0 to 3.5 | 0.0 to 4.5 |
| Dorsal Raphe Nucleus | 0.0 to 0.5 | −0.2 to −1.0 | −1.0 to −2.0 |
| Nucleus Accumbens | 0.5 to 3.0 | −1.0 to 2.0 | 1.0 to 3.0 |
| Frontal Cortex | 0.0 to 5.0 | 2.0 to −2.5 | 4.0 to 7.0 |
| Locus Coeruleus | 0.3 to 1.0 | −1.8 to −3.0 | −1.2 to −2.5 |

In the foregoing table: the medial-lateral dimensions are relative to midline of the brain; the anterior-posterior dimensions are relative to the midpoint between the anterior commissure and posterior commissure with negative indicating the posterior direction; the dorsal-ventral dimensions are relative to a line connecting the midpoints of the anterior and posterior commissures with negative being ventral to; all dimensions are in centimeters.

Alternatively, these agents might be infused into the lateral ventricle or third ventricle of the brain or just beneath the dura above the cortex or in the intrathecal space. In this instance the drug would diffuse to the appropriate site of action.

Exemplary liquid agents which provide the desired actions identified in Table I, ranges of dosages and concentrations for the liquid agents are provided in the following Table III:

TABLE III

| DRUG CLASS | SPECIFIC DRUG | DOSING RANGE |
|---|---|---|
| Glutamate Agonist | D-Cycloserine | 1–10 muM |
| | L-AP4 | 1–10 muM |
| | Carboxyphenylglycine | 10–500 muM |
| | L-glutamic acid | 1–100 muM |
| | cis-Piperidine-2,3- dicarboxylic acid | 1–10 muM |
| | (+/−)-trans-ACPD | 1–10 muM |
| | L-AP4 | 1–10 muM |
| Glutamate Antagonists | MK801(dizocilpine) | 1–20 muM |
| | ketamine Hcl | 5–50 muM |
| | AP-3 | 1–10 muM |
| | Dextromethorphan | 1–100 muM |
| | MCPD | 0.02–10 muM |
| | dextrorphan tartrate | 1–100 muM |
| | CNQX | 1–100 muM |
| GABA Agonists | baclofen | 0.1–10 muM |
| | muscinol HBr | 100–500 muM |
| GABA Antagonists | Gabazine | 1–50 muM |
| | Saclofen | 0.5–25 muM |
| | Bicuulline | 1–100 muM |
| | picrotoxin | 10–100 muM |
| Dopamine Antagonist | (+) apomorphine Hcl | 5–20 muM |
| | spiperone Hcl | 0.1–10 muM |
| | haloperidol | 10–100 muM |
| | (−) Sulpiride | 0.05–1 muM |
| Dopamine Agonist | methanesulfonate | 1–10 muM |
| | (−) apomorphine pergolide | 10–30 muM |
| Anesthetic | Lidocaine hydrochloride | 5–20 muM |
| Serotonin agonist | | |
| Serotonin antagonist | | |
| Adrenergic agonist | clonidine | |
| Adrenergic antagonist | | |

In Table II, muM means millimicromolar.

Microprocessor 100 within device 10 can be programmed so that a controlled amount of drug described in Table III can be delivered to the specific brain sites described in Table I.

The applicant has discovered that anxiety disorders, including phobias, panic attacks, and obsessive compulsions can be treated by electrically stimulating brain tissue either alone or while drugs are being administered as described above. The stimulation can be achieved by an ITREL II signal generator implemented as signal generator 16 (FIG. 1).

Electrical stimulation of neural tissue may be implemented by providing pulses to electrodes 38 and 40 (FIG. 3) preferably having amplitudes of 0.1 to 20 volts, pulse widths varying from 0.02 to 1.5 milliseconds, and repetition rates preferably varying from 2 to 2500 Hz. Pulses with the selected characteristics are then delivered from signal generator 16 through cable 42, catheter 22, tube 22A and electrodes 38 and 40 to the targeted tissue within brain B. The appropriate stimulation pulses are generated by signal generator 16 based on the programmed values established by the clinician. The type of stimulation administered by signal generator 16 to the brain depends on the specific location at which the electrodes 38 and 40 of tube 22A are surgically implanted and the desired action on the neurons at that location. If the neruonal activity is to be blocked, signal generator 16 will be programmed with a frequency preferably in the range 50 to 2500 HZ. If the neuronal activity is to be facilitated, the stimulus frequency is chosen preferably in the range of 2 to 100 Hz.

The appropriate stimulation for use in connection with the specific locations of the brain in which tube 22A terminates, together with the effect of the stimulation on that portion of the brain for a depressive disorder is provided in the following Table IV:

TABLE IV

| BRAIN LOCATION | DESIRED ACTION | TYPES OF STIMULATION |
|---|---|---|
| TREATMENT OF MANIC SYMPTOMS | | |
| Anterior Limb of Interal Capsule | Decrease Neuronal activity | High Frequency |
| Head of the Caudate Nucleus / Nucleus Accumbens | Decrease Neuronal activity | High Frequency |
| Cingulum fibers | Decrease Neuronal activity | High Frequency |
| Cingulate Gyrus | Decrease Neuronal activity | High Frequency |
| Dorsal Medial Nucleus of Thalamus | Decrease Neuronal activity | High Frequency |
| Locus Coeruleous | Decrease Neuronal activity | High Frequency |
| Dorsal raphe Nucleus | Decrease Neuronal activity | High Frequency |
| Frontal Cortex | Decrease Neuronal activity | High Frequency |
| TREATMENT OF DEPRESSIVE SYMPTOMS | | |
| Anterior Limb of Internal Capsule | Increase Neuronal activity | Low Frequency |
| Head of the Caudate Nucleus / Nucleus Accumbens | Increase Neuronal activity | Low Frequency |
| Cingulum fibers | Increase Neuronal activity | Low Frequency |
| Cingulate Gyrus | Increase Neuronal activity | Low Frequency |
| Dorsal Medial Nucleus of Thalamus | Increase Neuronal activity | Low Frequency |
| Locus Coeruleous | Increase Neuronal activity | Low Frequency |
| Dorsal raphe Nucleus | Increase Neuronal activity | Low Frequency |
| Frontal Cortex | Increase Neuronal activity | Low Frequency |

TABLE IV-continued

Coordinates for the portions of the brain described in Table IV are given in Table II.

A microprocessor within signal generator 16 can be programmed so that the desired stimulation can be delivered to the specific brain sites described in Table IV.

The system shown in FIG. 1 is an open-loop system. The microcomputer algorithm programmed by the clinician sets the stimulation parameters of signal generator 16 and/or infusion rates of infusion pump 10. This algorithm may change the parameter values over time but does so independent of any changes in symptoms the patient may be experiencing. Alternatively, the closed-loop systems show in FIGS. 4–7 which incorporate sensor 130 to provide feedback could be used to provide enhanced results.

Figure 4:
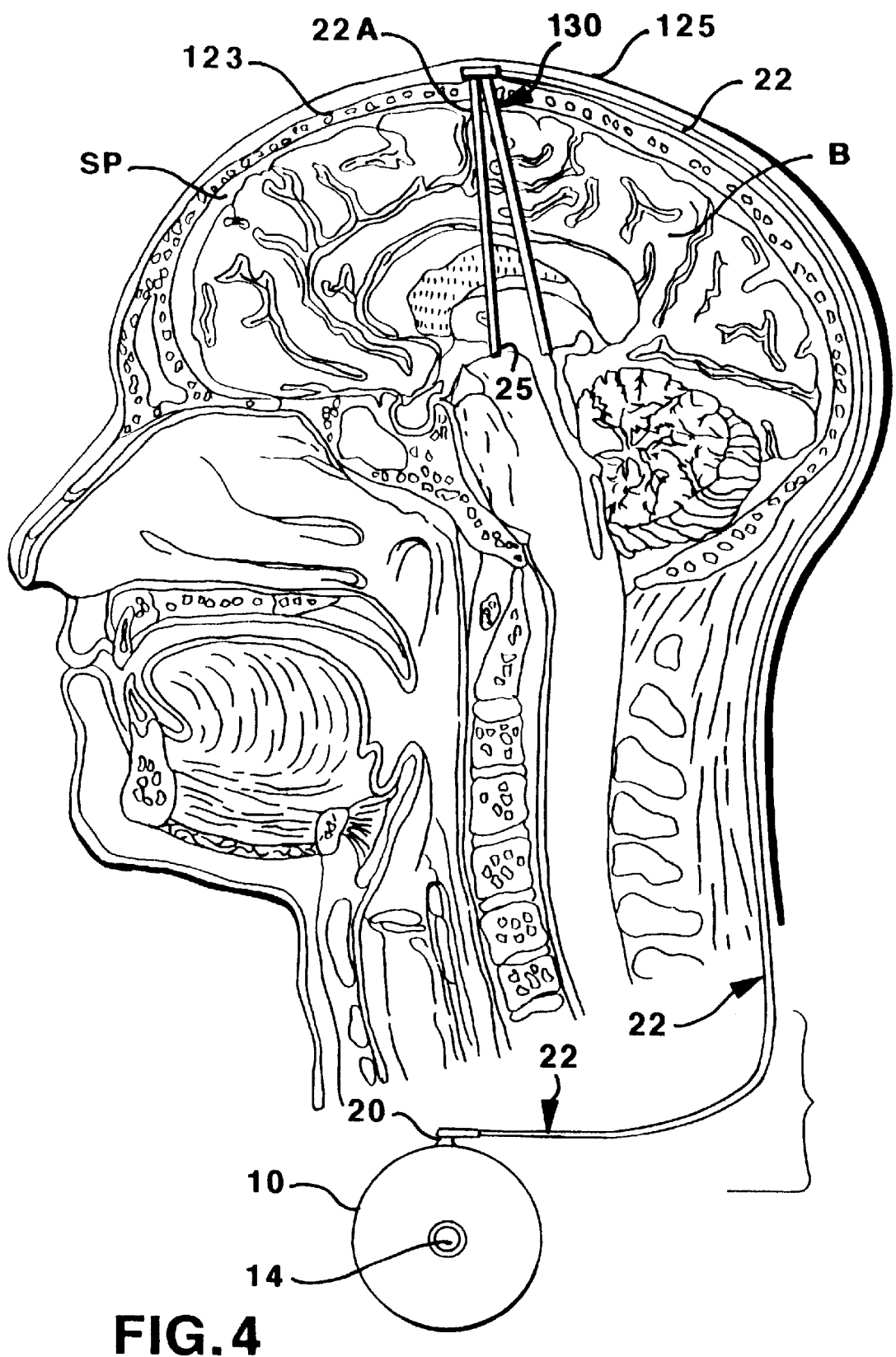
FIG. 4 is a diagrammatic illustration of a catheter and a sensor implanted in a brain and a pump coupled to the catheter and sensor.
Figure 5:
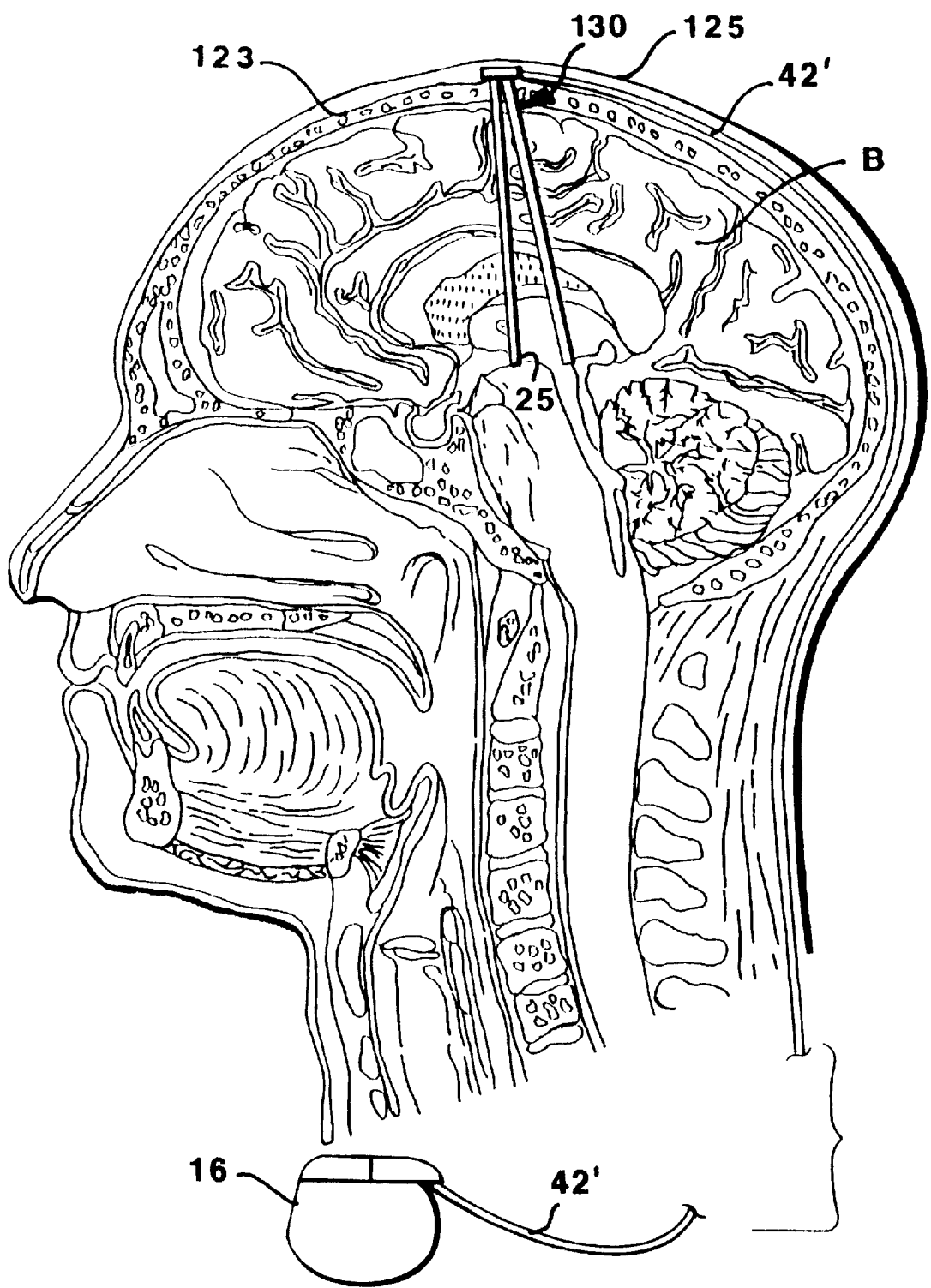
FIG. 5 is a diagrammatic illustration of a lead and a sensor implanted in a brain and a signal generator coupled to the lead and sensor.

FIG. 4 depicts an infusion pump 10 connected through tube 22 to a distal portion 22A and a separate sensor portion 130. FIG. 5 depicts a signal generator 16 connected through cable 42' which has a distal portion 42'A with electrodes 38 and 40 located at the distal end and a sensor portion 130. The devices in FIGS. 4 and 5 provide "closed-loop" infusion of medication and "closed-loop" stimulation respectively.

Figure 6:
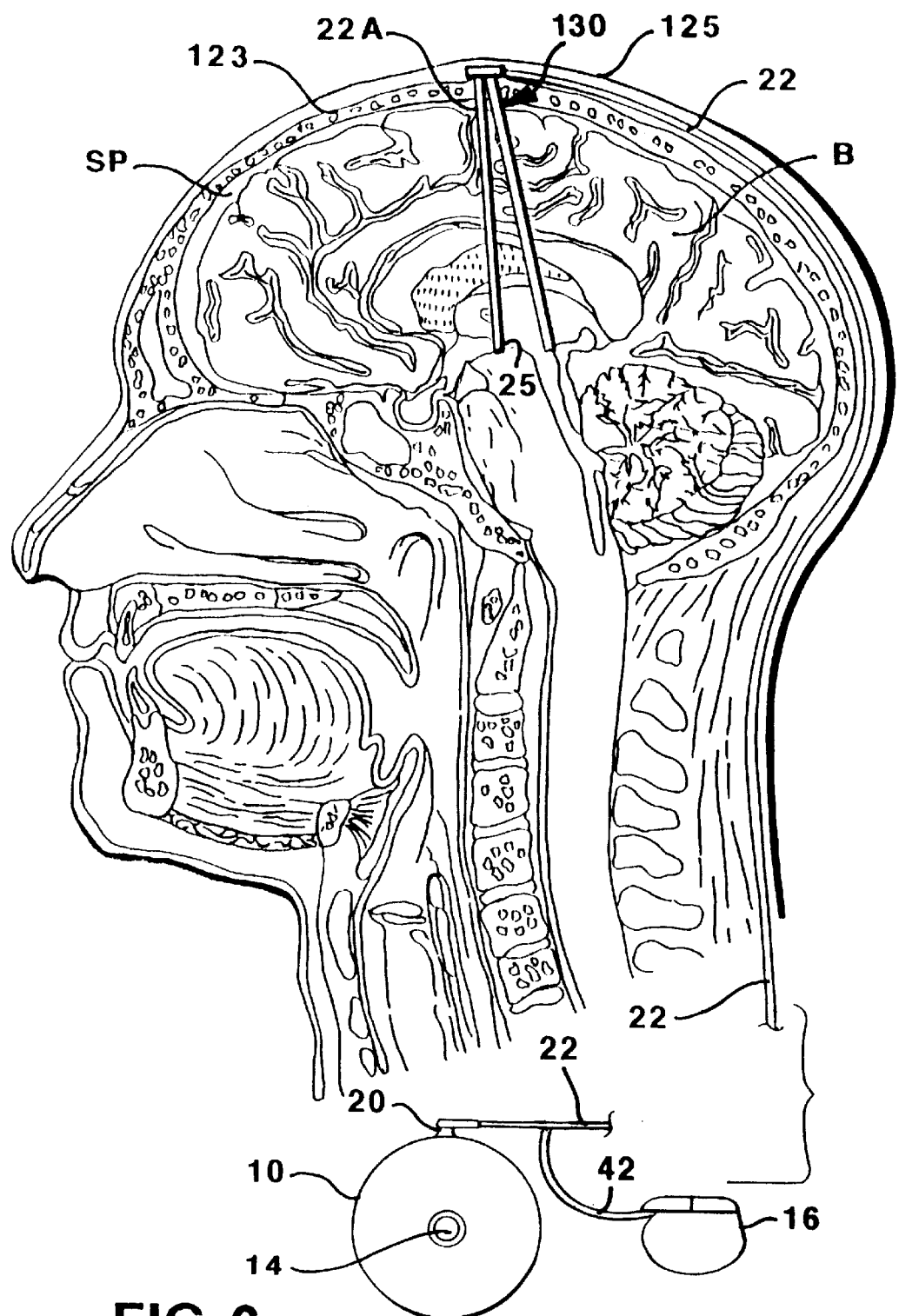
FIG. 6 is a diagrammatic illustration of a combined lead and catheter and a sensor implanted in a brain and a signal generator and pump coupled to the combined catheter and electrode and sensor.

Alternatively, the device in FIG. 6 allows for the combination of infusion and stimulation both therapies being controlled by a feed back sensor 130. In FIG. 6, the stimulation electrodes 38 and 40 are made a part of tube 22A as depicted in FIG. 3.

Figure 7:
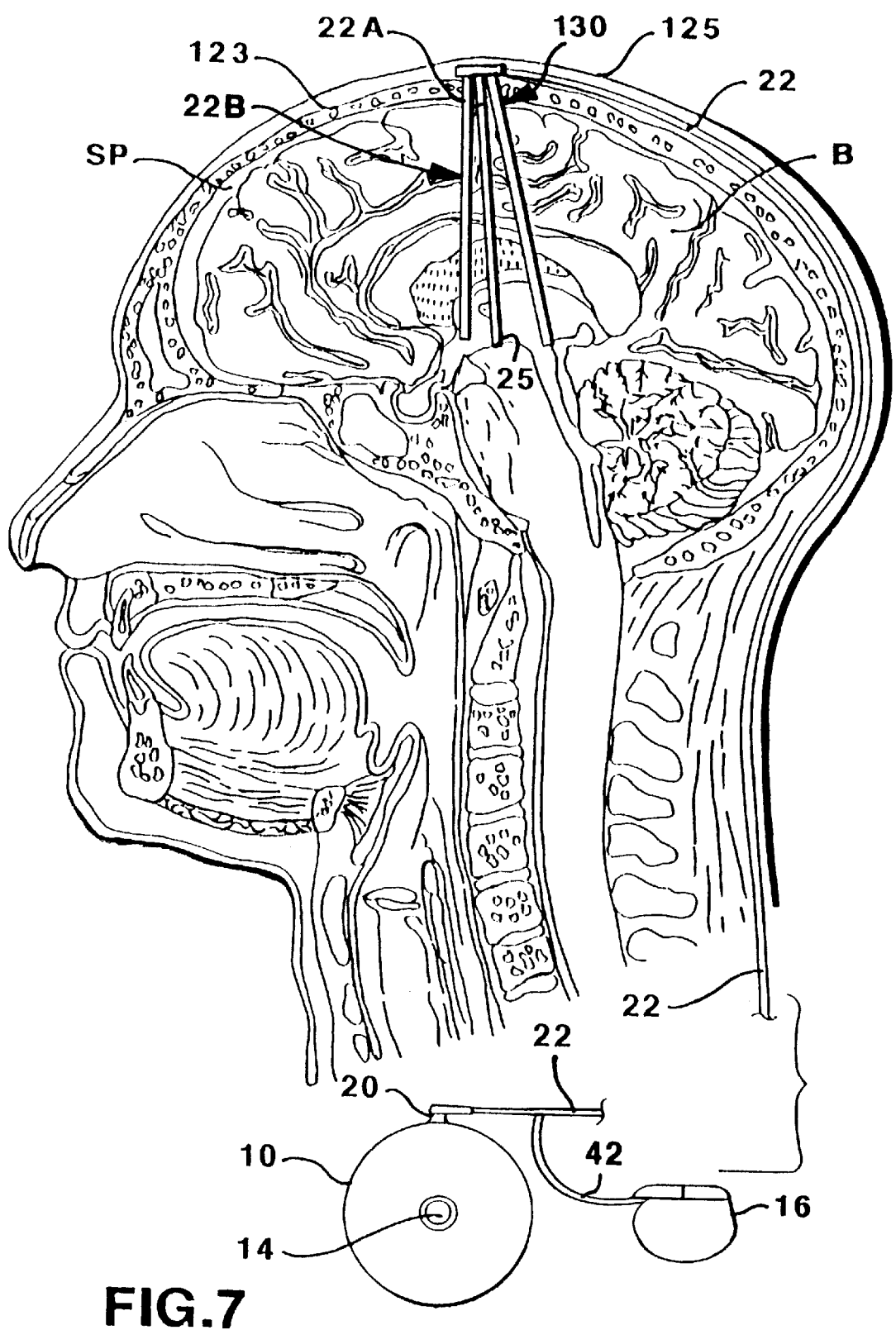
FIG. 7 is a diagrammatic illustration of a separate lead and catheter and a sensor implanted in a brain and a signal generator and pump coupled to the lead, catheter and sensor.

Alternatively, referring to FIG. 7 the stimulation electrodes 38 and 40 could be located on a separate tube 22B away from the microporous regions 27–29 located on tube 22A. This would allow delivery of stimulation to a different site in brain B than the site where medication is delivered. The sensor 130 is located at still a different site in brain B. Under certain circumstances it may be desirable to have sensor 130 phsically located on either tube 22A or tube 22B.

A sensor 130 is implanted into a portion of a patient's body suitable for detecting symptoms of the disorder being treated. Sensor 130 is adapted to sense an attribute of the symptom to be controlled or an important related symptom. For depressive disorders this could be abnormal electrical activity in one part of the brain such as those described in Table II. Alternatively, it could be abnormal concentrations of chemical substances in one location of the brain.

Brain EEG (e.g., cortical potentials recorded above the neurons controlling specific aspects of behavior associated with the neurological disorder) also may be detected by sensor 130. In this case, sensor 130 would take the form of an electrode with impedance values preferably chosen to optimize recording of electrical signals.

Yet another form of sensor 130 would include a device capable of detecting nerve compound action potentials.

Sensor 130 also may take the form of a device capable of detecting nerve cell or axon activity that is related to the pathways at the cause of the symptom, or that reflects sensations which are elicited by the symptom. Such a sensor may be located deep in the brain. For such detecting, sensor 130 may take the form of an electrode inserted into the internal capsule, cortex or basal ganglia of the brain. Signals of any kind that are received by the sensor may by amplified before transmission to circuitry contained within device 10 or device 16.

Sensor 130 may take the form of a transducer consisting of an electrode with an ion selective coating applied which is capable of directly transducing the amount of a particular transmitter substance or its breakdown by-products found in the interstitial space of a region of the brain such as the nucleus accumbens. The level of the interstitial transmitter substance is an indicator of the relative activity of the brain region. An example of this type of transducer is described in the paper "Multichannel semiconductor-based electrodes for in vivo electrochemical and electrophysiological studies in rat CNS" by Craig G. van Horne, Spencer Bement, Barry J. Hoffer, and Greg A. Gerhardt, published in *Neuroscience Letters,* 120 (1990) 249–252.

Sensor 130 may be external to the body communicating with the implanted portions through telemetry. An example of an external sensor is an electrical device that includes an electrode attached to the surface of the skin which passes a small current to measure the skin impedence. An example of this type of sensor is described in the paper "Skin Impedance in Telation to Pain Threshold Testing by Electrical Means", by Emily E. Meuller, Robert Loeffel and Sedgwick Mead, published in J. Applied Physiology 5, 746–752, 1953. A decrease in skin impedence may indicate an increase in anxiety.

Figure 8:
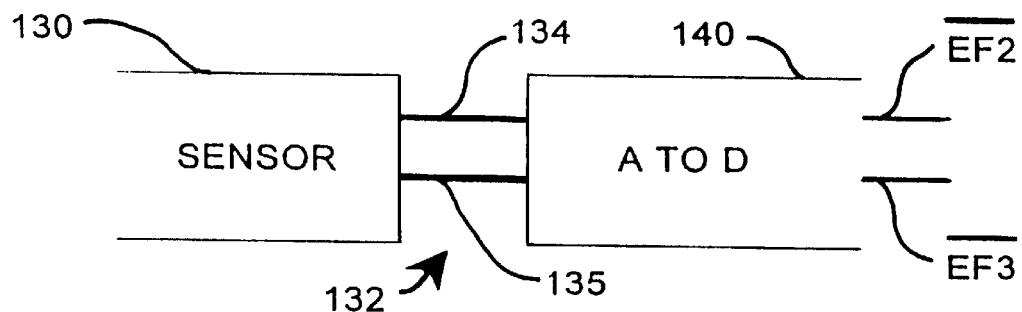
FIG. 8 is a schematic block diagram of a sensor and analog to digital converter circuit used in the preferred embodiment of the invention.
Figure 9:
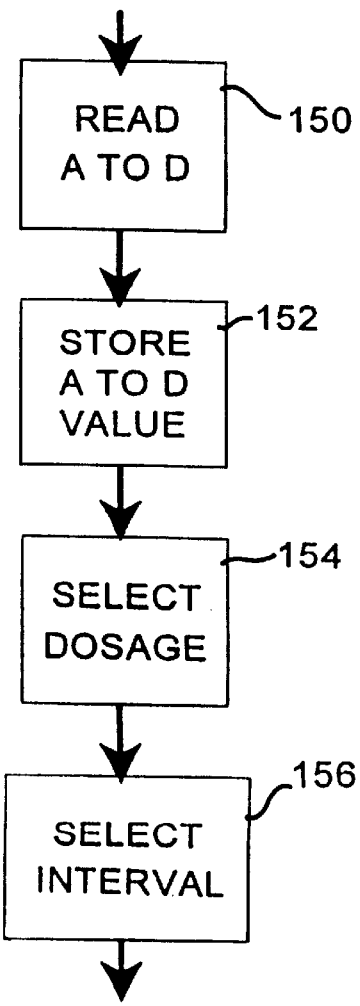
FIG. 9 is a flow chart illustrating a preferred form of a microprocessor program for utilizing the sensor to control drug dosage administered to the brain.

Other sensors such as Carbon dioxide gas sensors or other sensors that can detect the physiological parameters such as those listed above will be clear to those skilled in the art. Referring to FIG. 8, the output of sensor 130 is coupled by a cable 132 comprising conductors 134 and 135 to the input of analog to digital converter 140. Alternatively, the output of an external feedback sensor would communicate with the implanted pulse generator or pump through a telemetry downlink. The output of the analog to digital converter is connected to terminals EF2 BAR and EF3 BAR shown in FIG. 11A of U.S. Pat. No. 4,692,147 ("'147 Patent"). Before converter 140 is connected to the terminals, the demodulator 101 currently shown in FIG. 11A would be disconnected. A drug can be delivered essentially continuously (within the constraints of the particular delivery device being used) or it may be delivered during intermittent intervals coordinated to reflect the half-life of the particular agent being infused or with circadian rhythms. As an example, the symptoms of the neurological disorder may normally subside at night when the person is sleeping so the drug delivery rates might be reduced to coincide with the hours between 10 p.m. and 7 a.m.

Microprocessor 100 within device 10 can be programmed so that a controlled amount of drug can be delivered to the specific brain sites described in Table I. Alternatively, sensor 130 can be used with a closed loop feedback system in order to automatically determine the level of drug delivery necessary to alleviate the symptoms of the neurological disorder.

Figure 10:
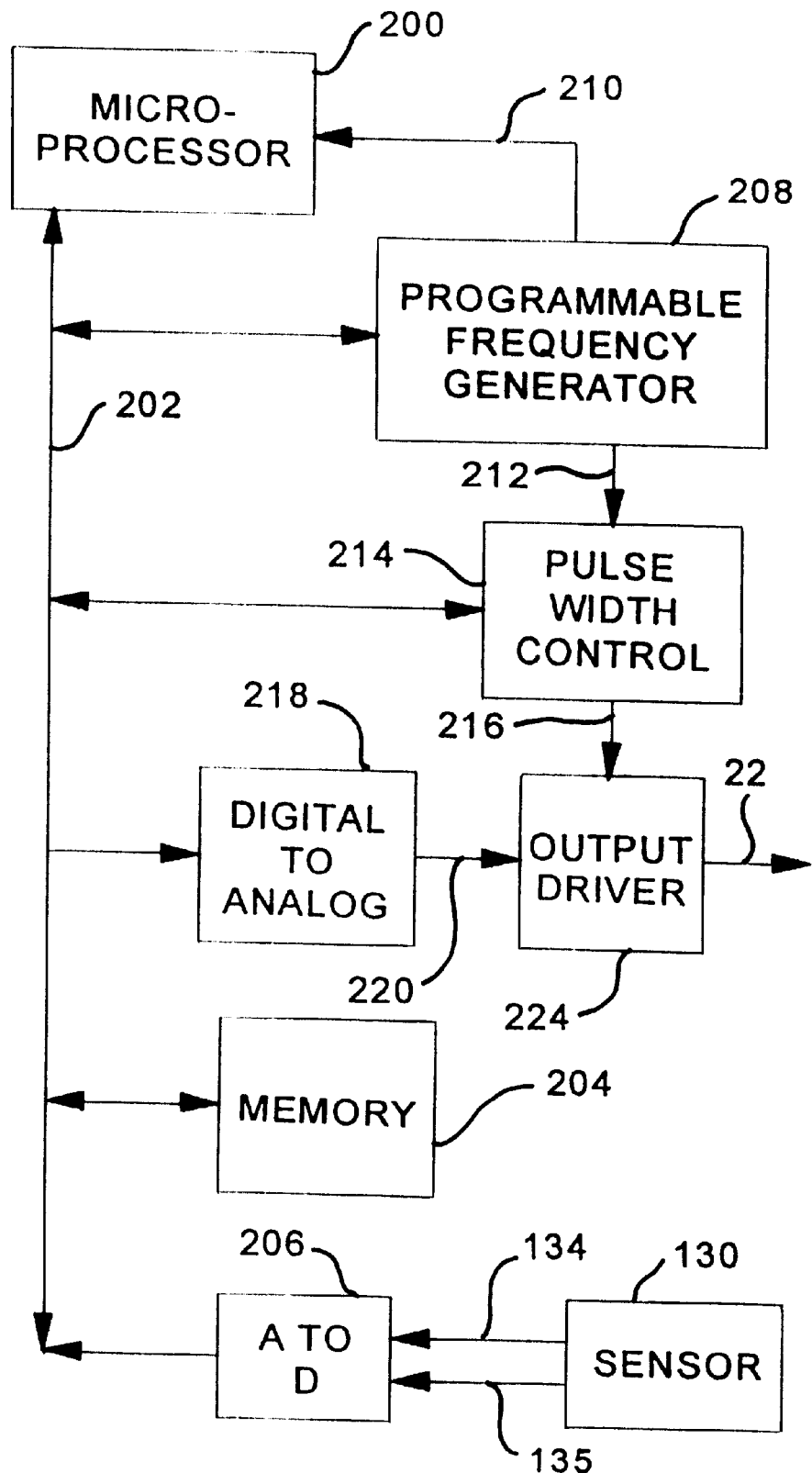
FIG. 10 is a schematic block diagram of a microprocessor and related circuitry for utilizing the sensor to control stimulation administered to the brain.

The applicants have discovered that the efficacy of treatment may be enhanced if the neural tissue is stimulated while drugs are being administered as described above. The stimulation can be achieved by a modified form of the ITREL II signal generator implemented as signal generator 16 (FIG. 1) which is described in FIG. 10. The output of sensor 130 is coupled by cable 132, comprising conductors 134 and 135, to the input of an analog to digital converter 206. Alternatively, the output of an external sensor would communicate with the implanted pulse generator through a telemetry downlink.

For some types of sensors, a microprocessor and analog to digital converter will not be necessary. The output from sensor 130 can be filtered by an appropriate electronic filter in order to provide a control signal for signal generator 16. An example of such a filter is found in U.S. Pat. No. 5,259,387 "Muscle Artifact Filter, Issued to Victor de Pinto on Nov. 9, 1993.

The output of the analog to digital converter 206 is connected to a microprocessor 200 through a peripheral bus 202 including address, data and control lines. Microprocessor 200 processes the sensor data in different ways depending on the type of transducer in use. When the signal on sensor 130 exceeds a level programmed by the clinician and stored in a memory 204, increasing amounts of stimulation will be applied through an output driver 224.

The stimulus pulse frequency is controlled by programming a value to a programmable frequency generator 208 using bus 202. The programmable frequency generator provides an interrupt signal to microprocessor 200 through an interrupt line 210 when each stimulus pulse is to be generated. The frequency generator may be implemented by model CDP1878 sold by Harris Corporation.

The amplitude for each stimulus pulse is programmed to a digital to analog converter 218 using bus 202. The analog output is conveyed through a conductor 220 to an output driver circuit 224 to control stimulus amplitude.

Microprocessor 200 also programs a pulse width control module 214 using bus 202. The pulse width control provides an enabling pulse of duration equal to the pulse width via a conductor. Pulses with the selected characteristics are then delivered from signal generator 16 through cable 22 and lead 22A or 22B to the target locations of a brain B.

Microprocessor 200 executes an algorithm shown in FIGS. 11–15 in order to provide stimulation with closed loop feedback control. At the time the stimulation signal generator 16 or alternative device in which the stimulation and infusion functions are combined is implanted, the clinician programs certain key parameters into the memory of the implanted device via telemetry. These parameters may be updated subsequently as needed. Step 400 in FIG. 11 indicates the process of first choosing whether the neural activity at the stimulation site is to be blocked or facilitated (step 400(1)) and whether the sensor location is one for which an increase in the neural activity at that location is equivalent to an increase in neural activity at the stimulation target or vice versa (step 400(2)). Next the clinician must program the range of values for pulse width (step 400(3)), amplitude (step 400(4)) and frequency (step 400(5)) which signal generator 16 may use to optimize the therapy. The clinician may also choose the order in which the parameter changes are made (step 400(6)). Alternatively, the clinician may elect to use default values.

Figure 11:
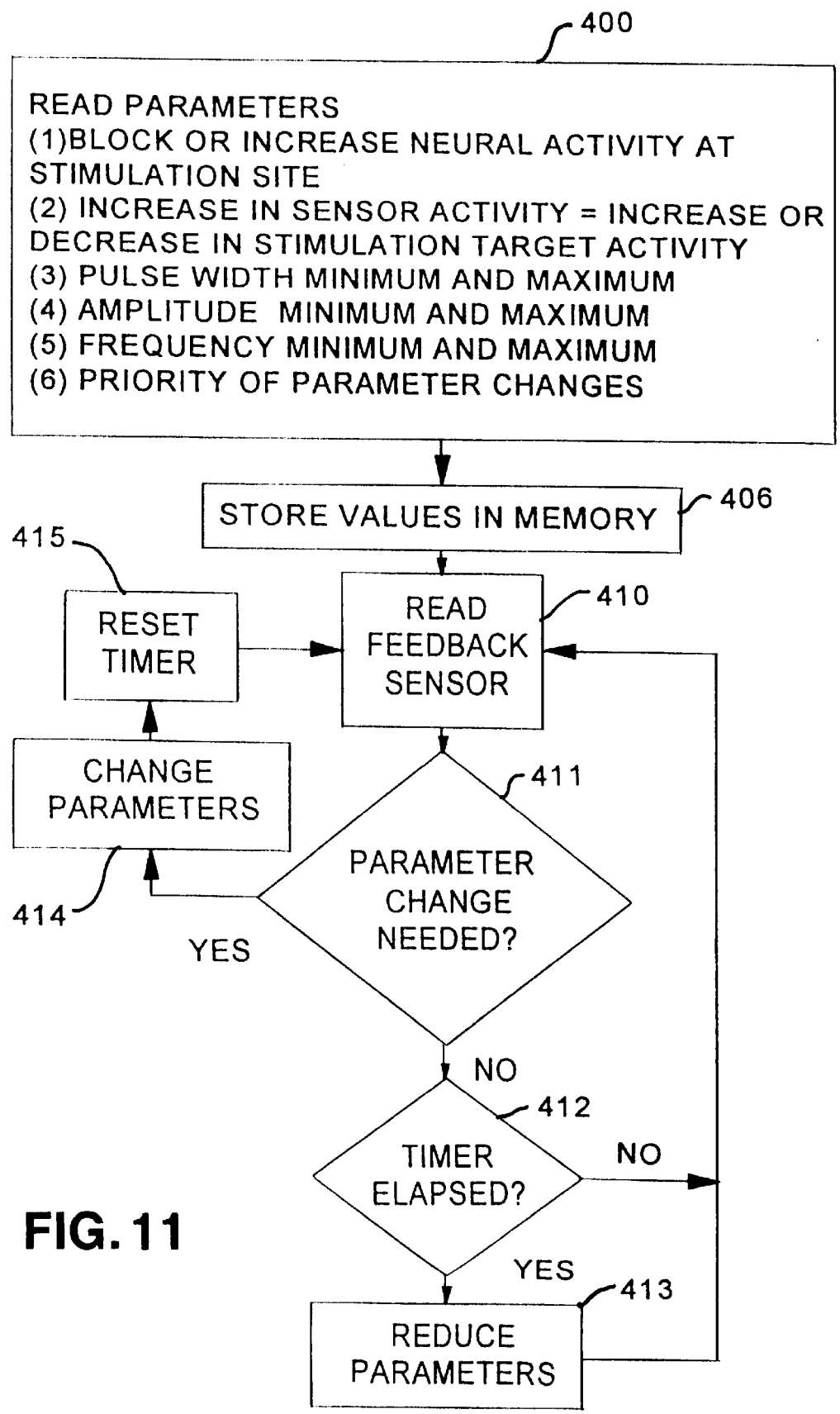
FIGS. 11–15 are flow charts illustrating a preferred form of microprocessor program for generating stimulation pulses to be administered to the brain.

The algorithm for selecting parameters is different depending on whether the clinician has chosen to block the neural activity at the stimulation target or facilitate the neural activity. FIG. 11 details steps of the algorithm to make parameter changes.

Figure 12:
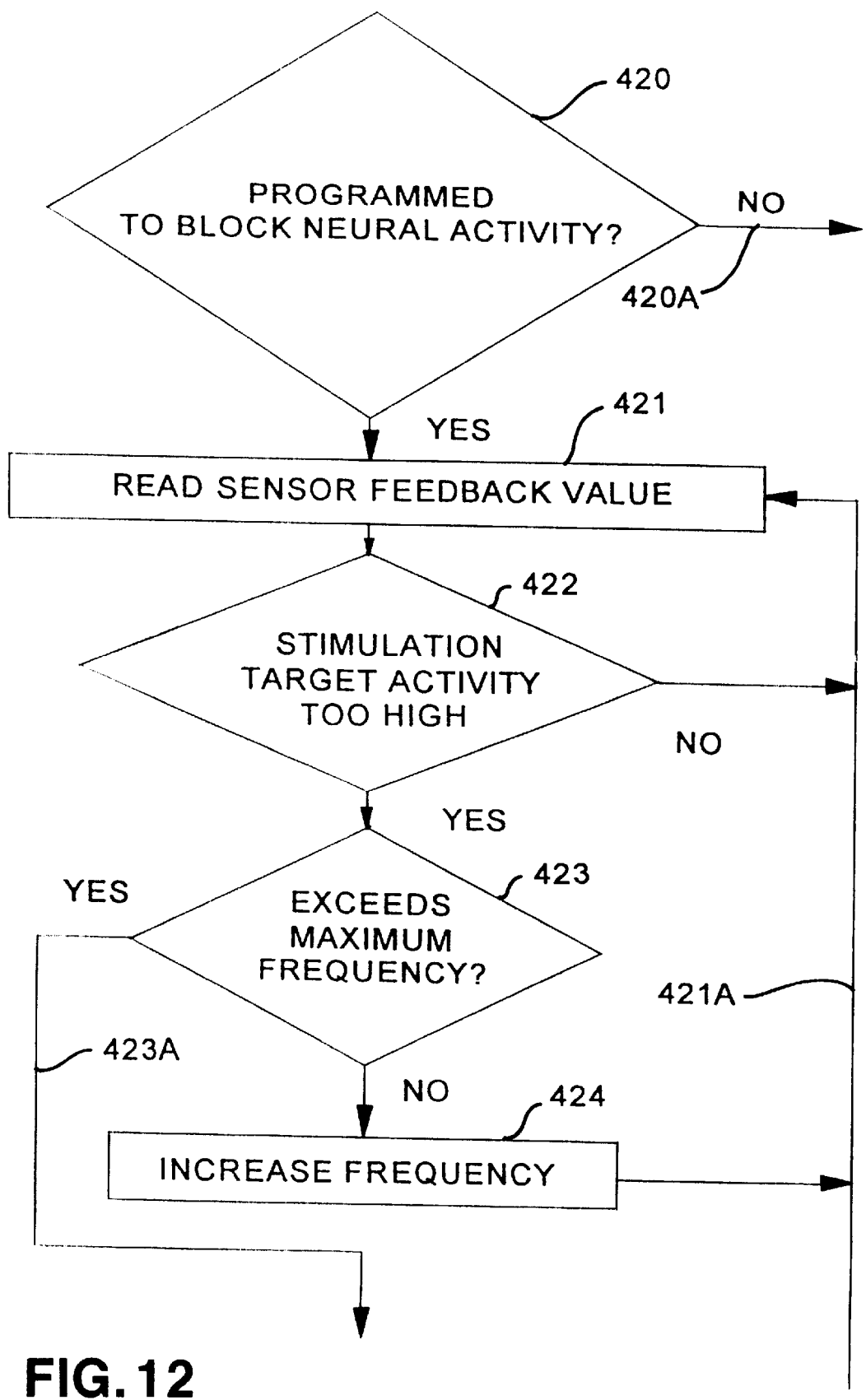
Figure 13:
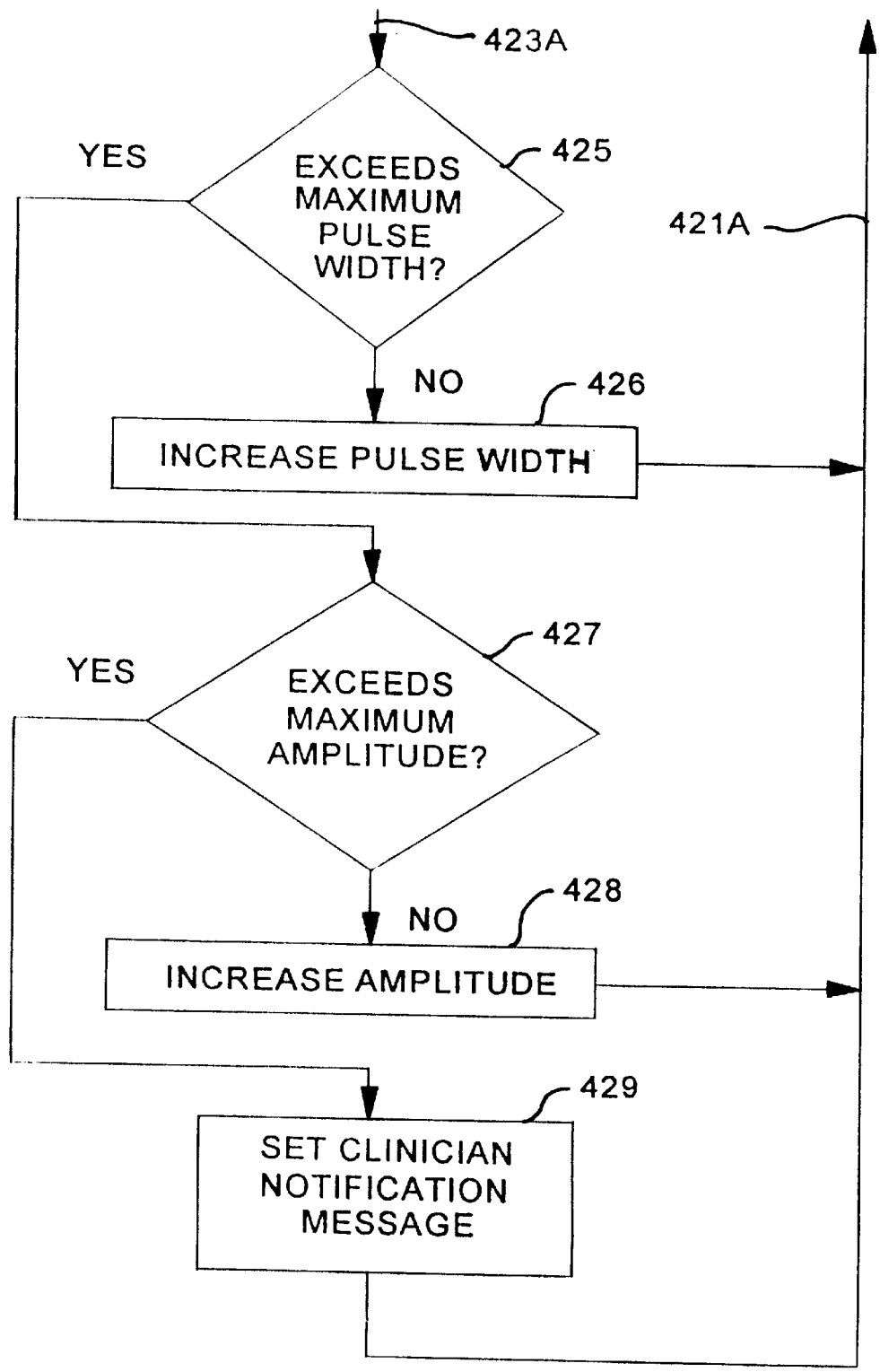
Figure 14:
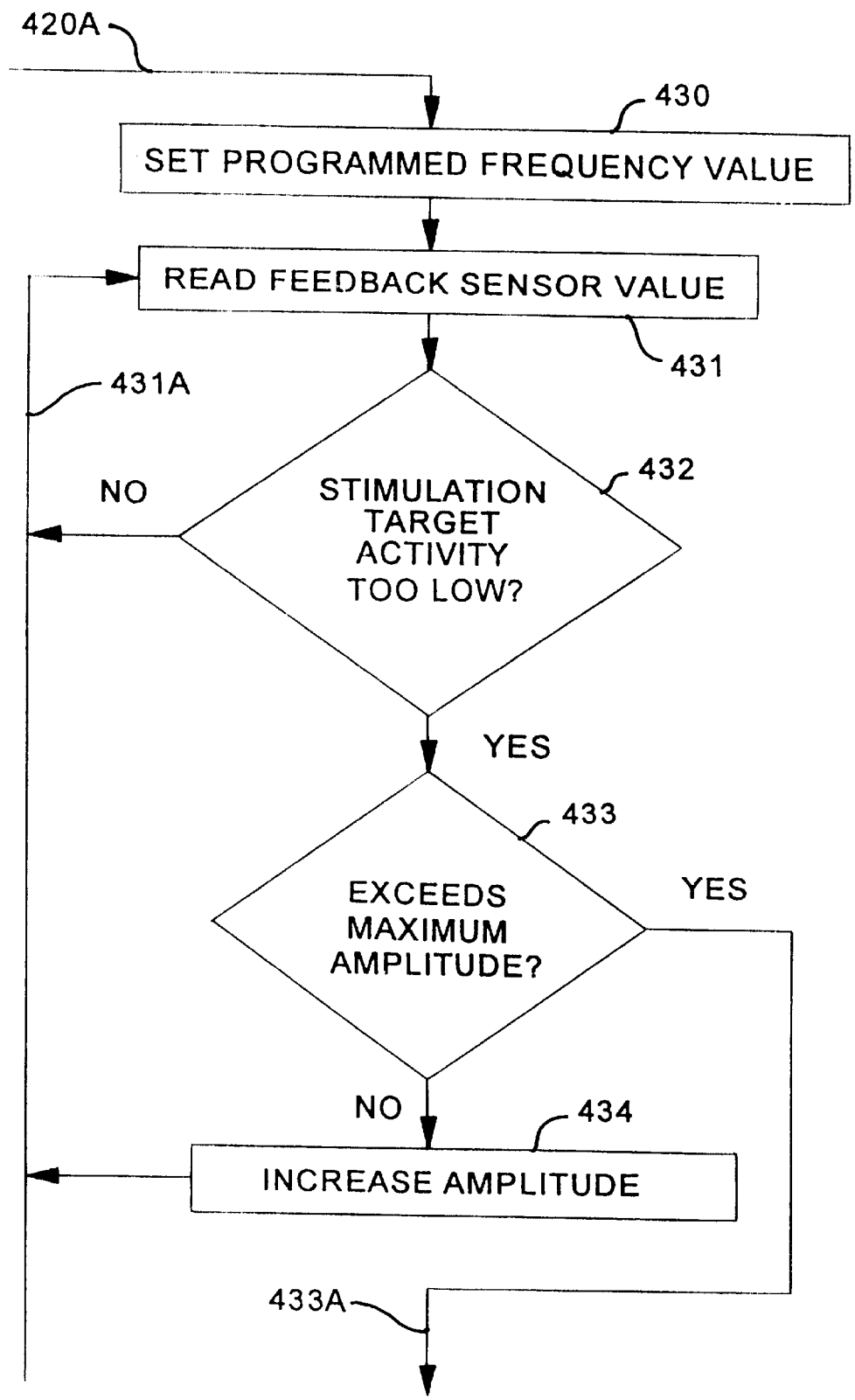

The algorithm uses the clinician programmed indication of whether the neurons at the particular location of the stimulating electrode are to be facilitated or blocked in order to decide which path of the parameter selection algorithm to follow (step 420, FIG. 12). If the neuronal activity is to be blocked, signal generator 16 first reads the feedback sensor 130 in step 421. If the sensor values indicate the activity in the neurons is too high (step 422), the algorithm in this embodiment first increases the frequency of stimulation in step 424 provided this increase does not exceed the preset maximum value set by the physician. Step 423 checks for this condition. If the frequency parameter is not at the maximum, the algorithm returns to step 421 through path 421A to monitor the feed back signal from sensor 130.

If the frequency parameter is at the maximum, the algorithm next increases the pulse width in step 426 (FIG. 13), again with the restriction that this parameter has not exceeded the maximum value as checked for in step 425 through path 423A. Not having reached maximum pulse width, the algorithm returns to step 421 to monitor the feedback signal from sensor 130. Should the maximum pulse width have been reached, the algorithm next increases amplitude in a like manner as shown in steps 427 and 428. In the event that all parameters reach the maximum, a notification message is set in step 429 to be sent by telemetry to the clinician indicating that device 16 is unable to reduce neural activity to the desired level.

Figure 15:
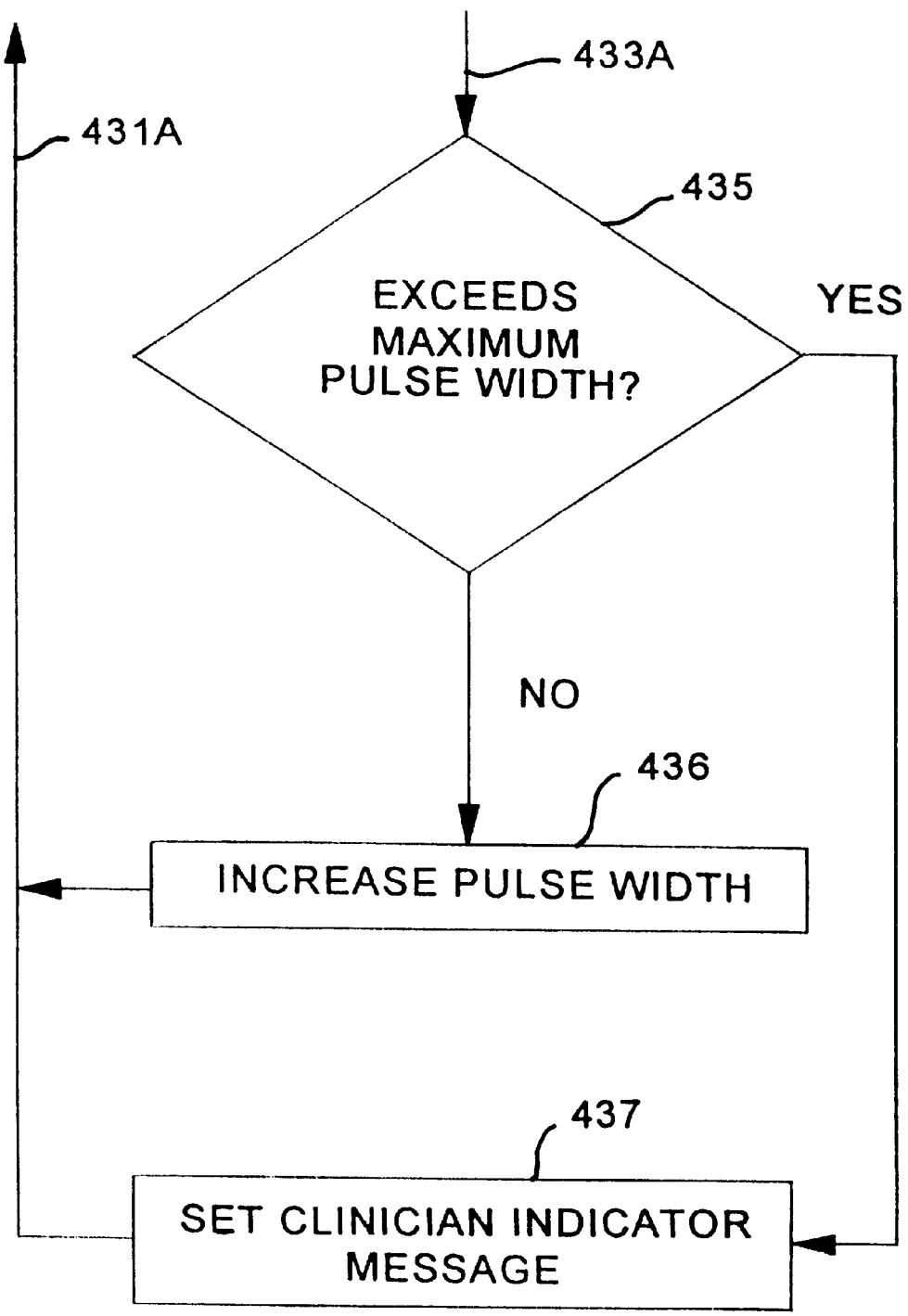

If, on the other hand, the stimulation electrode is placed in a location which the clinician would like to activate in order to alter the symptoms of the neurological disorder, the algorithm would follow a different sequence of events. In the preferred embodiment, the frequency parameter would be fixed at a value chosen by the clinician to facilitate neuronal activity in step 430 (FIG. 14) through path 420A. In steps 431 and 432 the algorithm uses the values of the feedback sensor to determine if neuronal activity is being adequately controlled. In this case, inadequate control indicates that the neuronal activity of the stimulation target is too low. Neuronal activity is increased by first increasing stimulation amplitude (step 434) provided it doesn't exceed the programmed maximum value checked for in step 433. When maximum amplitude is reached, the algorithm increases pulse width to its maximum value in steps 435 and 436 (FIG. 15). A lack of adequatealteration of the symptoms of the neurological disorder, even though maximum parameters are used, is indicated to the clinician in step 437. After steps 434, 436 and 437, the algorithm returns to step 431 through path 431A, and the feedback sensor again is read.

It is desirable to reduce parameter values to the minimum level needed to establish the appropriate level of neuronal activity in, for example, the target brain nucleus. Superimposed on the algorithm just described is an additional algorithm to readjust all the parameter levels downward as far as possible. In FIG. 11, steps 410 through 415 constitute the method to do this. When parameters are changed, a timer is reset in step 415. If there is no need to change any stimulus parameters before the timer has counted out, then it may be possible due to changes in neuronal activity to reduce the parameter values and still maintain appropriate levels of neuronal activity in the target neurons. At the end of the programmed time interval, signal generator 16 tries reducing a parameter in step 413 to determine if control is maintained. If it is, the various parameter values will be ratcheted down until such time as the sensor values again indicate a need to increase them. While the algorithms in FIGS. 11–15 follow the order of parameter selection indicated, other sequences may be programmed by the clinician.

Figure 17:
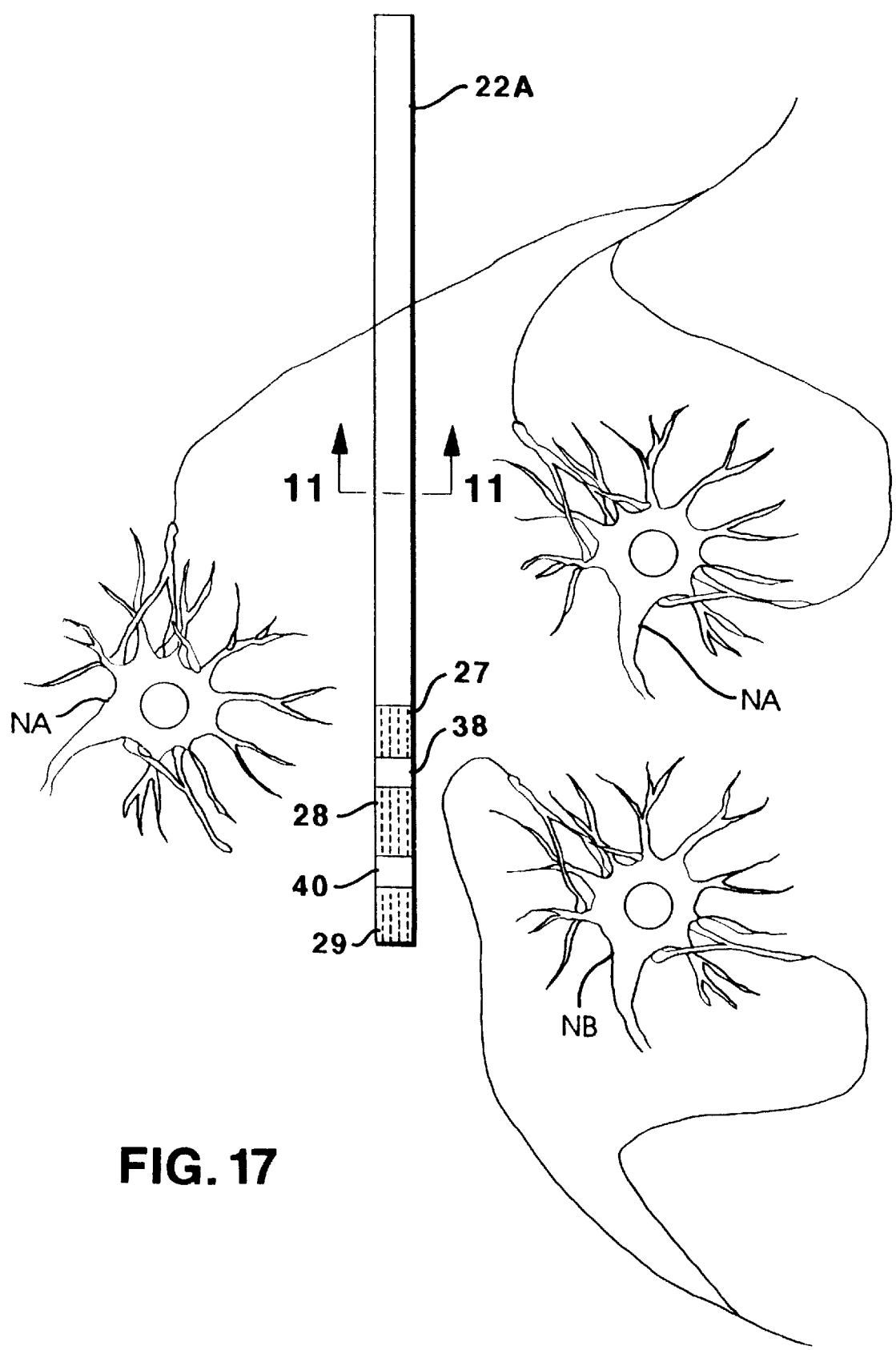
FIGS. 17–21 are diagrammatical views of the catheter-electrode shown in FIG. 1 arranged adjacent various types of neural tissue.

The foregoing techniques for simultaneous drug infusion and electrical stimulation can be applied to neural tissue in general, and are not limited to the previously described locations in the brain. FIG. 17 describes one such application in which type A neurons, such as NA, are located in the same region as type B neurons, such as NB which can typically be found in a brain. By infusing various agents through portions 27–29, neurons NA can be inhibited or excited with respect to their response to electrical stimulation provided by electrodes 38 and 40, while neurons NB remain unchanged with respect to their response to such stimulation. Thus, neurons NA or NB can be selectively stimulated by electrodes 38 and 40 due to the infusion of substances through portions 27–29 of tube 22A.

Figure 18:
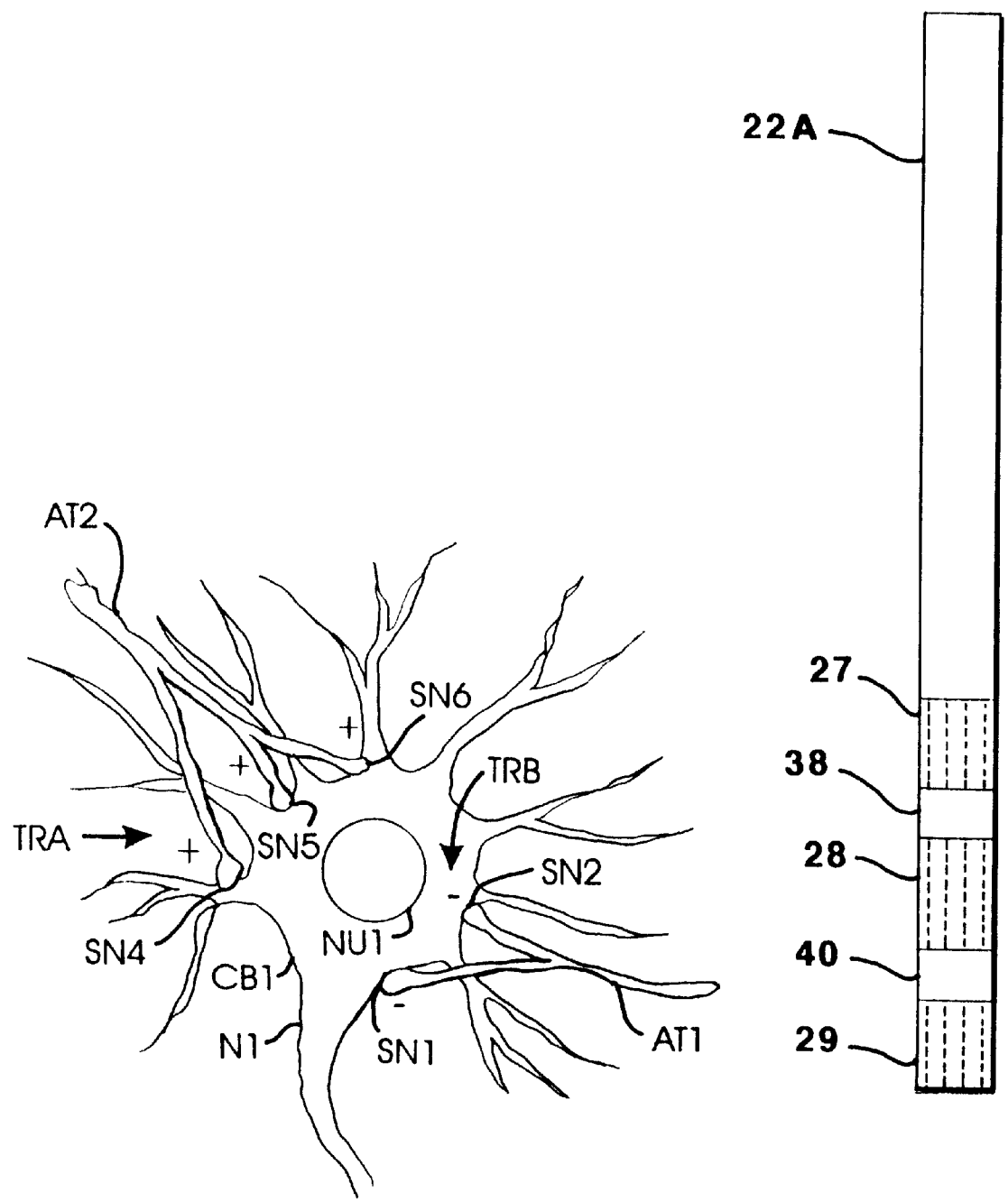

Referring to FIG. 18, a neuron N1 found in a brain has a cell body CB1 and a nucleus NU1. Neuron N1 can be excited by axon terminals AT1 at synapses SN1–SN2 by an inhibitory neurotransmitter TRB and can be excited by axon terminals AT2 at synapses SN4–SN6 by an excitatory neurotransmitter TRA. Portions 27–29 are used to infuse into the region of neuron N1 one or more of the following agents: an antagonist of transmitter TRB, an agonist of transmitter TRA, an agent to block the reuptake of transmitter TRA, a degradative enzyme for transmitter TRB and potassium. The agents can be infused separately or together in a cocktail. Such infusion leads to partial depolarization of neuron N1 and to a reduced threshold to stimulation by electrodes 38 and 40. That is, after infusion, the amplitude of stimulation required to create action potentials in neuron N1 is reduced compared to the time period before infusion.

Figure 19:
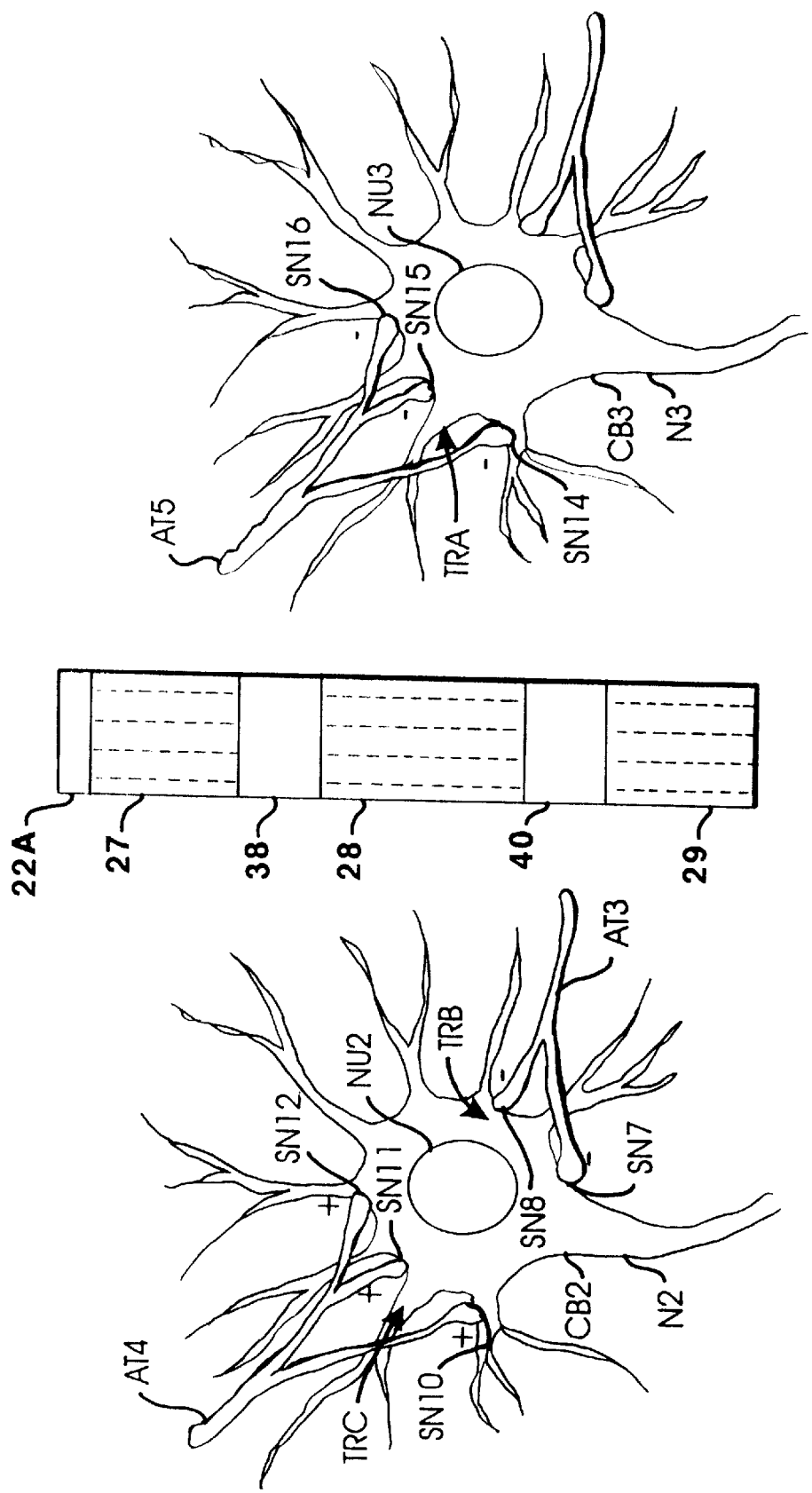

Referring to FIG. 19, a neuron N2 found in a brain has a cell body CB2 and a nucleus NU2. Neuron N2 can be inhibited by axon terminals AT3 at synapses SN7–SN8 by an inhibitory neurotransmitter TRB and can be excited by axon terminals AT4 at synapses SN10–SN12 by an excitatory neurotransmitter TRC.

A neuron N3 found in a brain has a cell body CB3 and a nucleus NU3. Neuron N3 can be inhibited by axon terminals AT5 at synapses SN14–SN16 by an inhibitory neurotransmitter TRA. Portions 27–29 of tube 22A are used to infuse into the region of neurons N2 and N3 one or more of the following agents: an agonist of transmitter TRA, an agent to block the reuptake of transmitter TRA or an agent to block a degradative enzyme for transmitter TRA. Each of these agents hyperpolarize neuron N3 and increase the potential threshold required to create action potentials in neuron N3. Therefore, neuron N2 can be selectively activated by electrodes 38 and 40 so that an action potential is created in neuron N2 without creating an action potential in neuron N3.

Selective activation of neuron N2 also can be achieved by infusing into the region of neurons N2 and N3 one or more of the following agents: an agonist for transmitter TRC, an agent to block the reuptake of transmitter TRC, an agent to block the degrading enzyme for transmitter TRC, an antagonist for transmitter TRB, an agent to enhance the reuptake of transmitter TRB or a degrading enzyme for transmitter TRB. The agents can be infused separately or together in a cocktail. Such infusion leads to partial depolarization of neuron N2 and to a reduced threshold to stimulation by electrodes 38 and 40. That is, after infusion, the amplitude of stimulation required to create action potentials in neuron N2 is reduced compared to the time period before infusion, making it easier to electrically stimulate neuron N2 relative to neuron N3.

Figure 20:
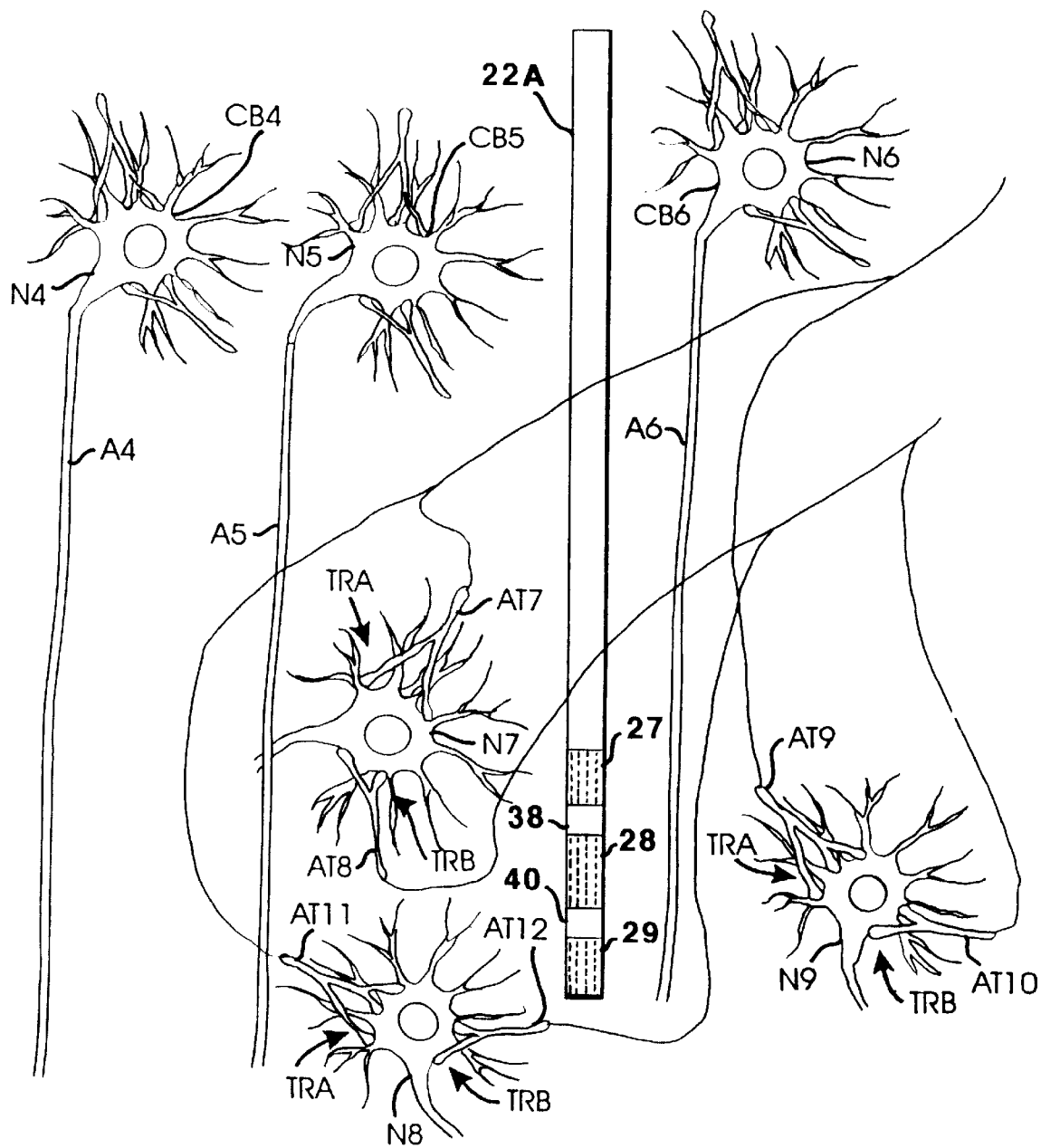

Referring to FIG. 20, neurons N4–N6 found in a brain have cells bodies CB4–CB6, respectively, and axons A4–A6, respectively, which are long fibers of passage that typically pass through white tissue in the spinal cord or brain. Cell bodies CB4–CB6 are located at portions of the body somewhat remote from infusion portions 27–29 and electrodes 38 and 40. However, portions of axons A4–A6 pass in the region of infusion portions 27–29 and electrodes 38 and 40. Neurons N7–N9 have cell bodies that are located in the region of infusion portions 27–29 and electrodes 38 and 40. Neuron N7 can be inhibited at axon terminals AT7 by an inhibitory neurotransmitter TRA and excited at axon terminals AT8 by an excitatory neurotransmitter TRB; neuron N9 can be inhibited at axon terminals AT9 by inhibitory neurotransmitter TRA and excited at axon terminals AT10 by excitatory neurotransmitter TRB; and neuron N8 can be inhibited at axon terminals AT11 by inhibitory neurotransmitter TRA and excited at axon terminals AT12 by an excitatory neurotransmitter TRB. Portions 27–29 are used to infuse an agonist of transmitter TRA, a reuptake blocker to transmitter TRA, a degrading enzyme blocker to transmitter TRA or an antagonist or degrading enzyme to transmitter TRB to raise the stimulation threshold of neurons N7–N9. Neurons N4–N6 are not affected by the infusion and can be selectively activated by stimulation supplied by electrodes 38 and 40.

Figure 21:
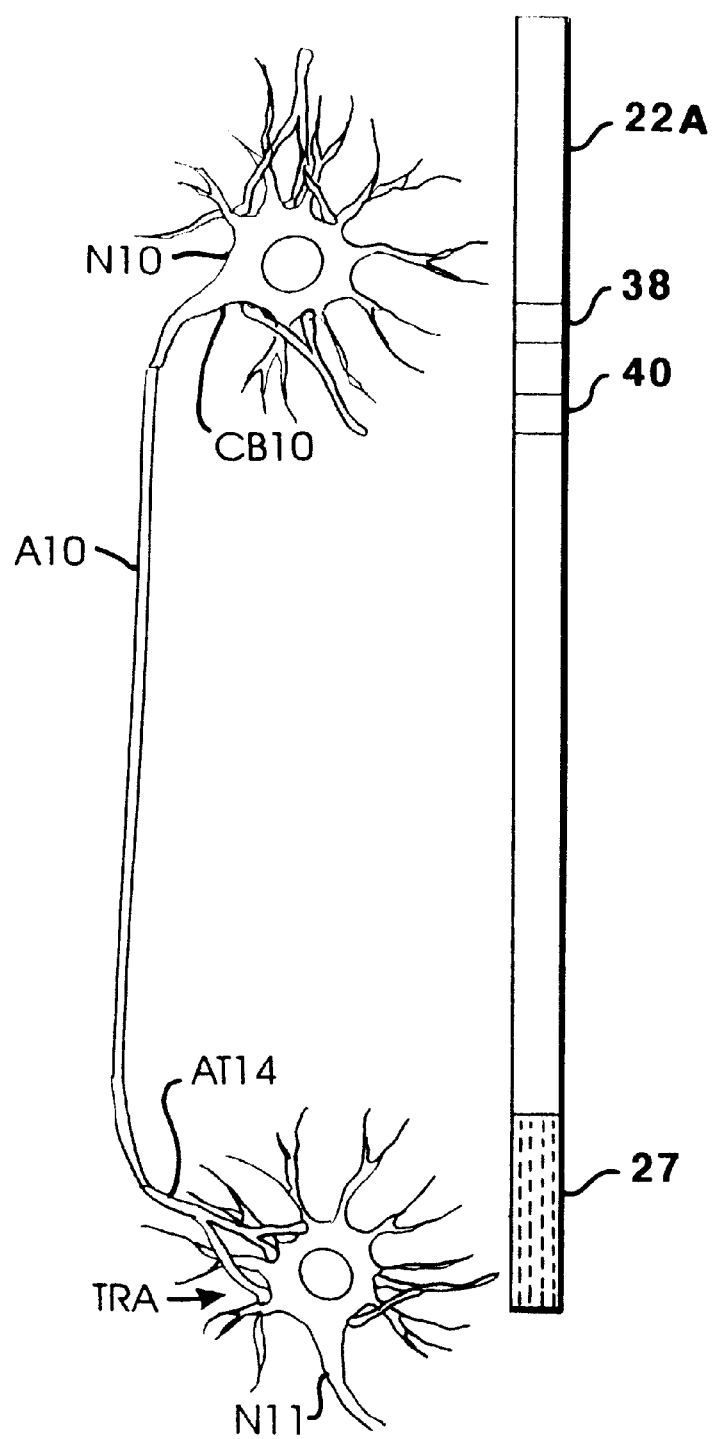

FIG. 21 illustrates a modified form of tube 22A in which infusion portion 27 is located more than 0.01 cm from electrodes 38 and 40 and infusion portions 28–29 have been removed. Neuron N10 has a cell body CB10 and an axon A10 that terminates in axon terminals AT14. A neuron N11 can be excited at axon terminals AT14 by an excitatory neurotransmitter TRA. Electrical stimulation of axon A10 causes the release of transmitter TRA at axon terminal AT14. Portion 27 is used to infuse an agent that blocks a degradative enzyme of transmitter TRA or an agent which blocks the reuptake of transmitter TRA. For each pulse administered by electrodes 38 and 40, the stimulation of neuron N11 is more potent. That is, more action potentials are generated in neuron N11.

Figure 16A:
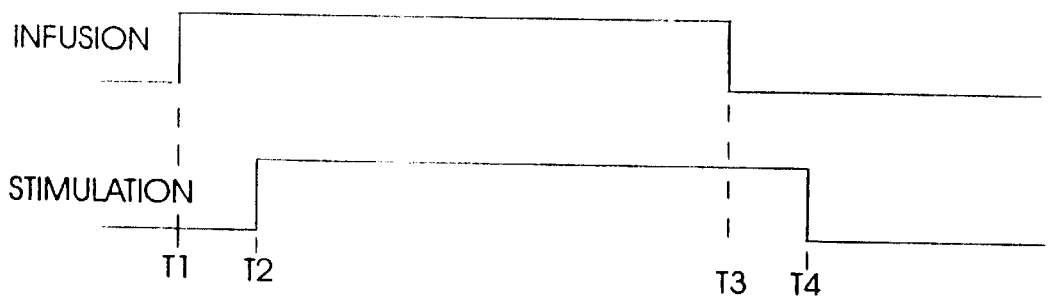
FIGS. 16A–16C are timing diagrams showing the relationship between the administration of drugs and electrical stimulation to nerve tissue.

FIG. 16A illustrates various times at which infusion and stimulation can be applied by tube 22A. For example, infusion alone can be applied from time T1 to T2, infusion and stimulation can be both be applied from time T2 to T3, and stimulation alone can be applied from time T3 to T4. This regimen might be used in the case when selective activation of one neuronal population is desired. By beginning the infusion before beginning stimulation during time T1 to T2, the threshold for electrical activation of one population of neurons can be lowered or raised as needed. Another example would be if a precursor molecule, such as L-dopa, is infused to guard against depletion of the transmitter substance dopamine.

Figure 16B:
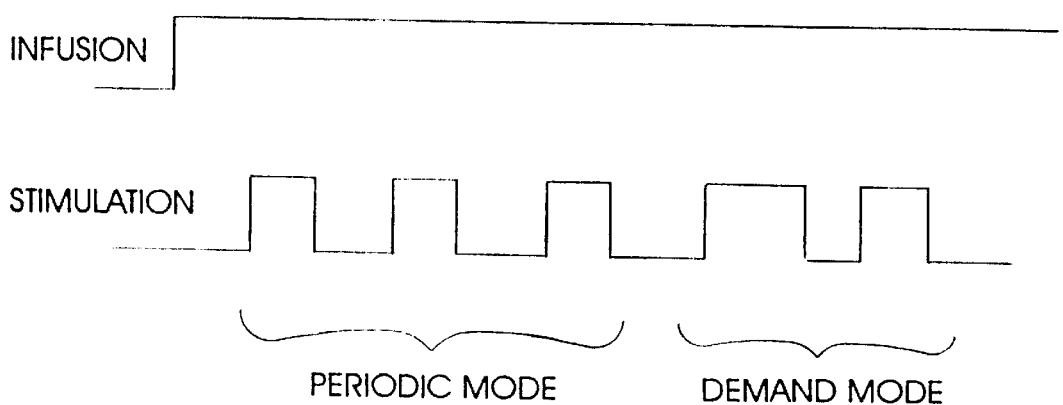

The stimulation might be applied periodically during the period of infusion either routinely or in response to sensor or patient generated demand as shown in FIG. 16B. Alternatively, stimulation could be applied continuously with infusion occuring periodically. Patient activation of either infusion or stimulation may occur as a result of an increase in symptoms being experienced by the patient.

Figure 16C:
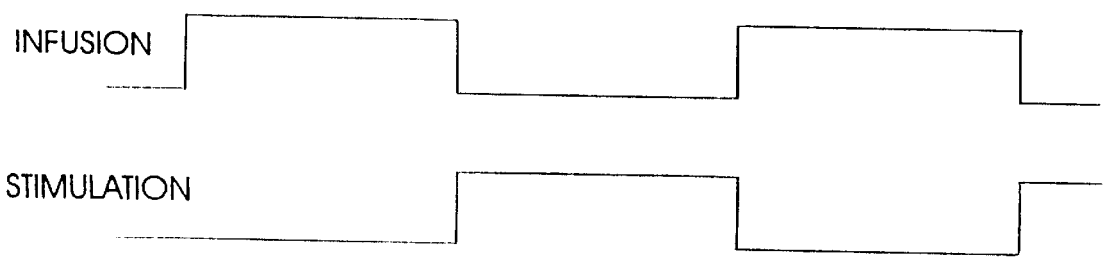

Alternatively, the infusion of an agent to activate a neuronal population might be alternated with application of electrical stimulation of that same population, as shown in FIG. 16C.

It also is possible to infuse an agent that has an affect upon the neuron population that is not strictly connected in time with the electrical depolarization of the neurons. In this case, the time of application of stimulation and infusion may be completely asynchronous. Or an agent could be infused that diffuses beyond the effects of the electrical stimulation but still has an advantageous effect on the brain independent of the stimulation effects.

In those instances where a continuous infusion of liquid agent is effective, the infusion device may be replaced with a static device such as is described in U.S. Pat. No. 4,892,538 which is incorporated by reference. An example of a static device is a device having a semipermeable wall enclosing encapsulated cells capable of secreting the appropriate agent. Alternatively, an implantable device could consist of a polymeric insert with the agent embedded within or on the surface of the polymer in such a way as to be slowly eluted from the polymer over time. Such a device is described in U.S. Pat. No. 4,346,709 "Drug Delivery Devices Comprising Errodable Polymer and Errosion Rate Modifier", Edward Schmitt Inventor, Issued Aug. 31, 1982, incorporated by reference and in U.S. Pat. No. 5,330,768 "Long-term Sustained Release Preperation." Yoshiya Yamahira et. al. Inventors, Issued Sep. 27, 1988. These alternative techniques could be employed with or without the simultaneous application of open-loop or closed-loop stimulation in the aforementioned manner.

By using the foregoing techniques for simultaneous drug infusion and electrical stimulation, depressive disorders including the sypmtoms of depression and mania can be controlled with a degree of accuracy previously unattainable. Those skilled in that art will recognize that the preferred embodiments may be altered or amended without departing from the true spirit and scope of the invention, as defined in the accompanying claims.

I claim:

1. A method of using one or more drugs to therapeutically treat depression and manic depression by means of an implantable pump and a catheter having a proximal end coupled to the pump and a discharge portion for infusing therapeutic dosages of the one or more drugs, as well as an electric signal generator and an implantable electrode having a proximal end and a stimulation portion, the method comprising the steps of:

surgically implanting the electrode so that the stimulation portion lies adjacent a predetermined stimulation site in brain tissue, the stimulation site chosen as a location that, when electrically stimulated, reduces syptoms of depression and manic depression;

surgically implanting the catheter so that the discharge portion lies adjacent a predetermined infusion site in the brain tissue, the infusion site chosen as a location that, when therapeutic dosages of the one or more drugs are infused thereto, reduces symptoms of depression and manic depression;

coupling the proximal end of the electrode to the signal generator;

operating the signal generator to stimulate the stimulation site;

operating the pump to discharge a predetermined dosage of the one or more drugs through the discharge portion of the catheter into the infusion site while the signal generator is stimulating the stimulation site, whereby depression and manic depression are treated.

2. A method, as claimed in claim 1, wherein the stimulation site is selected from the group consisting of Anterior Limb of Internal Capsule, Head of the Caudate Nucleus/ Nucleus Accumbens, Cingulum fibers, Cingulate Gyrus, Dorsal Medial Nucleus of Thalamus, Locus Coeruleous, Dorsal raphe Nucleus, Frontal Cortex and Frontal Cortex.

3. A method, as claimed in claim 1, wherein the infusion site is selected from the group consisting of Anterior Limb of Internal Capsule, Nucleus Accumbens, Head of the Caudate Nucleus/Nucleus Accumbens, Cingulum fibers, Cingulate Gyrus, Dorsal Medial Nucleus of Thalamus, Locus Coeruleous, Dorsal raphe Nucleus, Frontal Cortex, Thalamus and Frontal Cortex.

4. A method, as claimed in claim 1, wherein the one or more drugs is selected from the group consisting of Anesthetic, GABA Agonist, GABA Antagonist, Dopamine Antagonist, Dopamie Agonist, Serotonin Antagonist, Serotonin Agonist, Glutamate Antagonist, Glutamate Agonist, Adrenergic Agonist and Adrenergic Antagonist.

5. A method of using one or more drugs to therapeutically treat depression and manic depression by means of an implantable pump and a catheter having a proximal end coupled to the pump and a discharge portion for infusing therapeutic dosages of the one or more drugs, the method comprising the steps of:

surgically implanting the catheter so that the discharge portion lies adjacent a predetermined infusion site in the brain tissue, the infusion site chosen as a location that, when therapeutic dosages of the one or more drugs are infused thereto, reduces symptoms of depression and manic depression; and operating the pump to discharge a predetermined dosage of the one or more drugs through the discharge portion of the catheter into the infusion site, whereby the depression and manic depression is treated.

6. A method as claimed in claim 5 wherein the infusion site is selected from the group consisting of Anterior Limb of Internal Capsule, Nucleus Accumbens, Head of the Caudate Nucleus/Nucleus Accumbens, Cingulum fibers, Cingulate Gyrus, Dorsal Medial Nucleus of Thalamus, Locus Coeruleous, Dorsal raphe Nucleus, Frontal Cortex, Thalamus and Frontal Cortex.

7. A method as claimed in claim 6 wherein the one or more drugs is selected from the group consisting of Anesthetic, GABA Agonist, GABA Antagonist, Dopamine Antagonist, Dopamie Agonist, Serotonin Antagonist, Serotonin Agonist, Glutamate Antagonist, Glutamate Agonist, Adrenergic Agonist and Adrenergic Antagonist.

8. A method of using electrical stimulation to therapeutically treat depression and manic depression by means of a signal generator and an implantable electrode having a proximal end and a stimulation portion, the method comprising the steps of:

surgically implanting the electrode so that the stimulation portion lies adjacent a predetermined stimulation site in brain tissue;

coupling the proximal end of the electrode to the signal generator; and operating the signal generator to stimulate the stimulation site, whereby the depression and manic depression is treated.

9. A method, as claimed in claim 8, wherein the stimulation site is selected from the group consisting of Anterior Limb of Internal Capsule, Head of the Caudate Nucleus/ Nucleus Accumbens, Cingulum fibers, Cingulate Gyrus, Dorsal Medial Nucleus of Thalamus, Locus Coeruleous, Dorsal raphe Nucleus, Frontal Cortex and Frontal Cortex.

* * * * *

UNITED STATES PATENT AND TRADEMARK OFFICE
CERTIFICATE OF CORRECTION

PATENT NO. : 6,176,242 B1
DATED : January 23, 2001
INVENTOR(S) : Mark T. Rise

It is certified that error appears in the above-identified patent and that said Letters Patent is hereby corrected as shown below:

<u>Title page,</u>
[73] Assignee: should read -- Medtronic, Inc. --

Signed and Sealed this

Twenty-eighth Day of August, 2001

Attest:

*Attesting Officer*

NICHOLAS P. GODICI
*Acting Director of the United States Patent and Trademark Office*